(12) United States Patent
Eidenschink et al.

(10) Patent No.: US 8,075,576 B2
(45) Date of Patent: Dec. 13, 2011

(54) CLOSURE DEVICE, SYSTEM, AND METHOD

(75) Inventors: Tracee Eidenschink, Wayzata, MN (US); Karl A. Jagger, Deephaven, MN (US); Daniel Tomaschko, Savage, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1509 days.

(21) Appl. No.: 11/509,105

(22) Filed: Aug. 24, 2006

(65) Prior Publication Data

US 2008/0051829 A1 Feb. 28, 2008

(51) Int. Cl.
*A61B 17/08* (2006.01)

(52) U.S. Cl. ........ 606/151; 606/139; 606/142; 606/144; 606/213; 606/157

(58) Field of Classification Search ................ 606/232, 606/151, 139–148, 219–220, 213, 28–31; 600/139–146, 585
See application file for complete search history.

(56) References Cited

U.S. PATENT DOCUMENTS

| | | | |
|---|---|---|---|
| 4,485,816 A | | 12/1984 | Krumme |
| 4,543,090 A * | | 9/1985 | McCoy ............... 604/95.05 |
| 4,579,118 A * | | 4/1986 | Failla ............... 606/158 |
| 5,222,976 A * | | 6/1993 | Yoon ............... 606/223 |
| 5,725,552 A | | 3/1998 | Kotula et al. |
| 5,846,261 A | | 12/1998 | Kotula et al. |
| 5,904,703 A | | 5/1999 | Gilson |
| 5,944,738 A | | 8/1999 | Amplatz et al. |
| 5,989,242 A * | | 11/1999 | Saadat et al. ............... 606/1 |
| 6,296,622 B1 * | | 10/2001 | Kurz et al. ............... 604/93.01 |
| 6,323,459 B1 | | 11/2001 | Maynard |
| 6,478,773 B1 * | | 11/2002 | Gandhi et al. ............... 604/113 |
| 6,514,237 B1 * | | 2/2003 | Maseda ............... 604/533 |
| 6,702,835 B2 | | 3/2004 | Ginn |
| 6,712,836 B1 | | 3/2004 | Berg et al. |
| 6,776,784 B2 | | 8/2004 | Ginn |
| 6,939,348 B2 | | 9/2005 | Malecki et al. |
| 7,097,653 B2 | | 8/2006 | Freudenthal et al. |
| 7,331,969 B1 * | | 2/2008 | Inganas et al. ............... 606/143 |
| 7,666,135 B2 * | | 2/2010 | Couvillon, Jr. ............... 600/146 |
| 2001/0047579 A1 * | | 12/2001 | Lee et al. ............... 29/447 |
| 2003/0045893 A1 | | 3/2003 | Ginn |
| 2003/0236531 A1 * | | 12/2003 | Couvillon, Jr. ............... 606/113 |
| 2004/0015187 A1 * | | 1/2004 | Lendlein et al. ............... 606/228 |
| 2004/0054322 A1 | | 3/2004 | Vargas |
| 2004/0073242 A1 | | 4/2004 | Chanduszko |
| 2004/0087982 A1 * | | 5/2004 | Eskuri ............... 606/153 |
| 2004/0092973 A1 | | 5/2004 | Chanduszko et al. |
| 2004/0093017 A1 | | 5/2004 | Chanduszko |

(Continued)

OTHER PUBLICATIONS

International Search Report. Jan. 21, 2008. 2 pgs.

*Primary Examiner* — Corrine M McDermott
*Assistant Examiner* — Mark Mashack
(74) *Attorney, Agent, or Firm* — Brooks, Cameron & Huebsch, PLLC

(57) ABSTRACT

The present disclosure relates generally to devices, systems and methods for use with cardiac defects. A closure device includes an elongate body with a first actuator segment and a second actuator segment associated with the elongate body that can be bent into a first predetermined position and then to a second predetermined position where the distal end and the proximal end are more closely positioned than when in the first predetermined position.

6 Claims, 16 Drawing Sheets

U.S. PATENT DOCUMENTS

| | | |
|---|---|---|
| 2004/0133236 A1 | 7/2004 | Chanduszko |
| 2004/0236170 A1 | 11/2004 | Kim |
| 2004/0249398 A1 | 12/2004 | Ginn |
| 2005/0021016 A1 | 1/2005 | Malecki et al. |
| 2005/0043759 A1 | 2/2005 | Chanduszko |
| 2005/0075665 A1 | 4/2005 | Brenzel et al. |
| 2005/0085693 A1* | 4/2005 | Belson et al. ............... 600/146 |
| 2005/0101984 A1 | 5/2005 | Chanduszko et al. |
| 2005/0107669 A1* | 5/2005 | Couvillon, Jr. ............... 600/146 |
| 2005/0119675 A1 | 6/2005 | Adams et al. |
| 2005/0131401 A1 | 6/2005 | Malecki et al. |
| 2005/0165439 A1 | 7/2005 | Weber et al. |
| 2005/0251154 A1 | 11/2005 | Chanduszko et al. |
| 2005/0251201 A1 | 11/2005 | Roue et al. |
| 2005/0267495 A1 | 12/2005 | Ginn et al. |
| 2005/0267524 A1* | 12/2005 | Chanduszko ............... 606/213 |
| 2005/0273135 A1* | 12/2005 | Chanduszko et al. ........ 606/213 |
| 2005/0273138 A1 | 12/2005 | To et al. |
| 2006/0069408 A1 | 3/2006 | Kato |
| 2006/0074410 A1 | 4/2006 | Malecki et al. |
| 2006/0122647 A1 | 6/2006 | Callaghan et al. |
| 2006/0212071 A1 | 9/2006 | Ginn et al. |
| 2007/0027466 A1* | 2/2007 | Ortiz et al. ............... 606/198 |
| 2007/0250036 A1* | 10/2007 | Volk et al. ............... 604/510 |

* cited by examiner

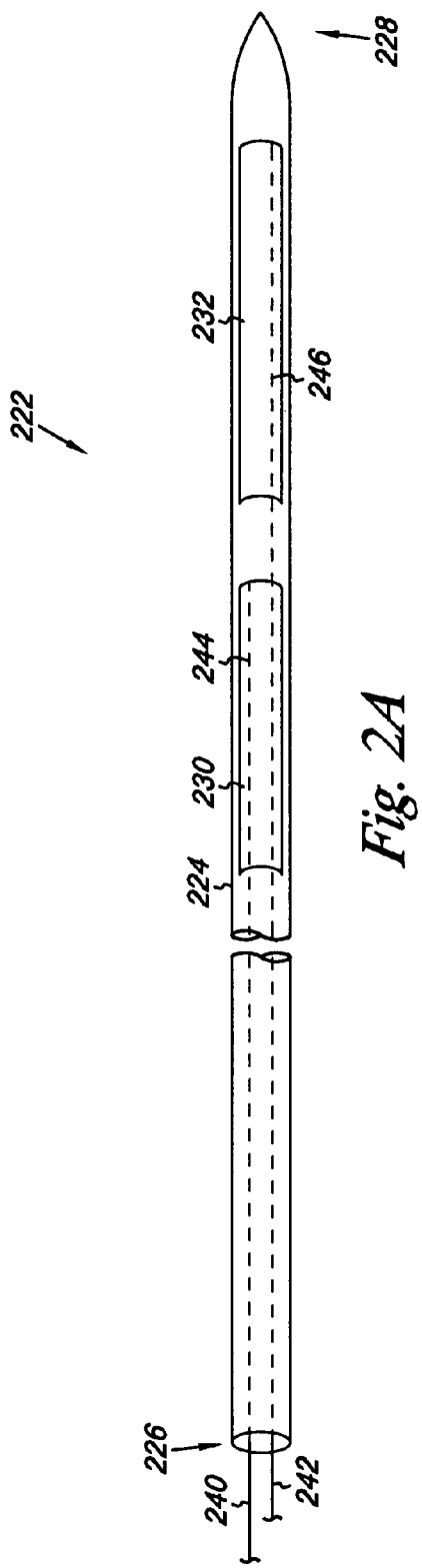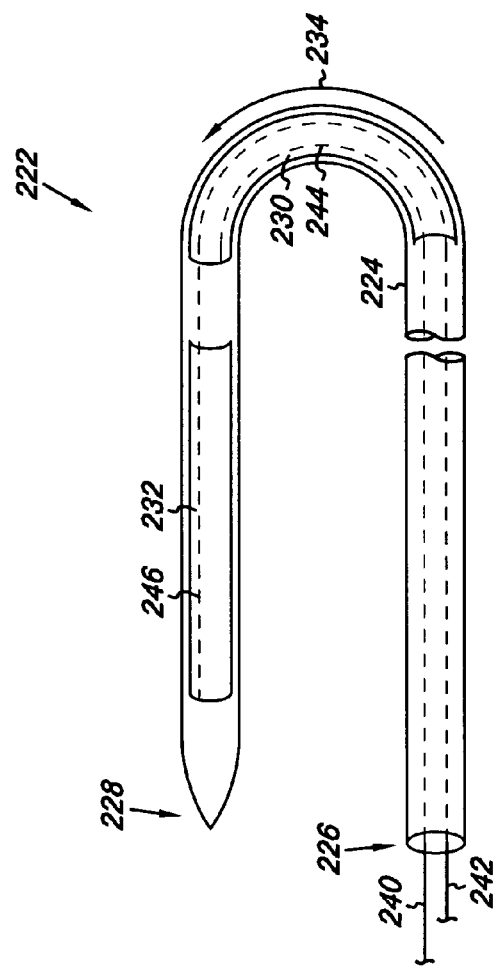

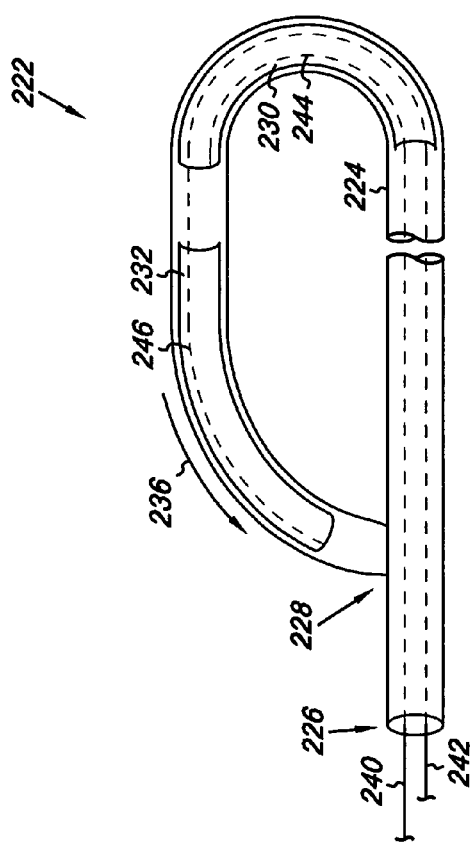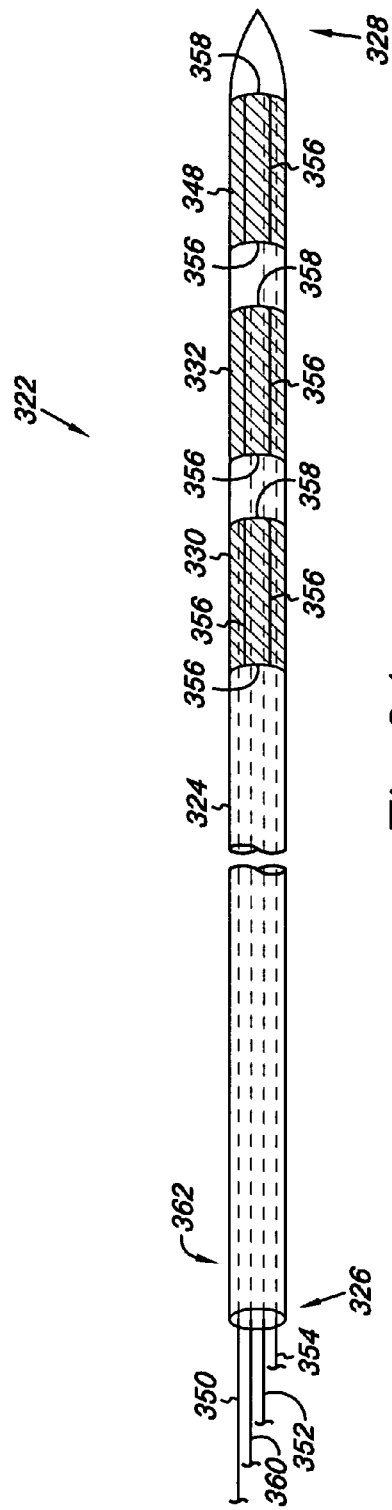

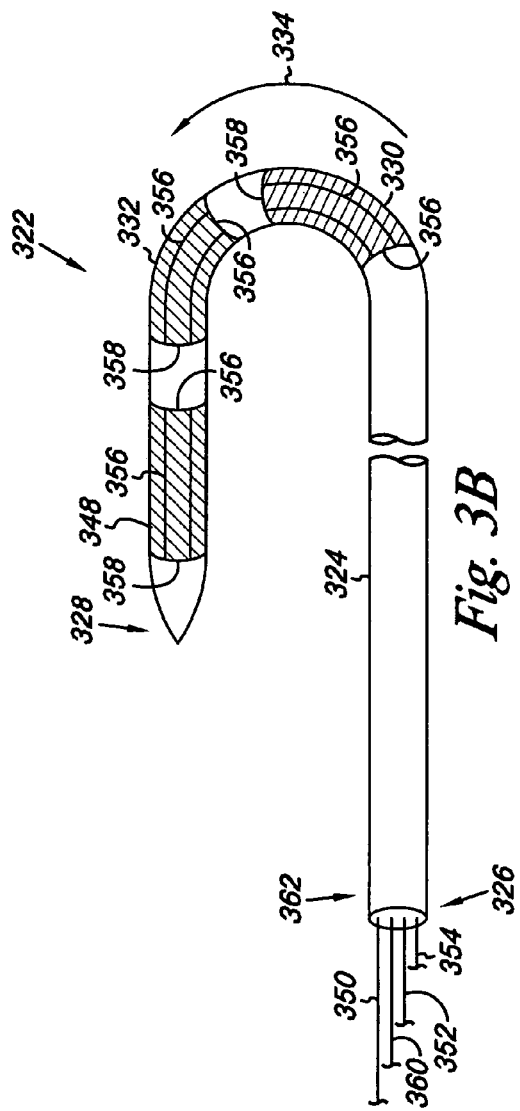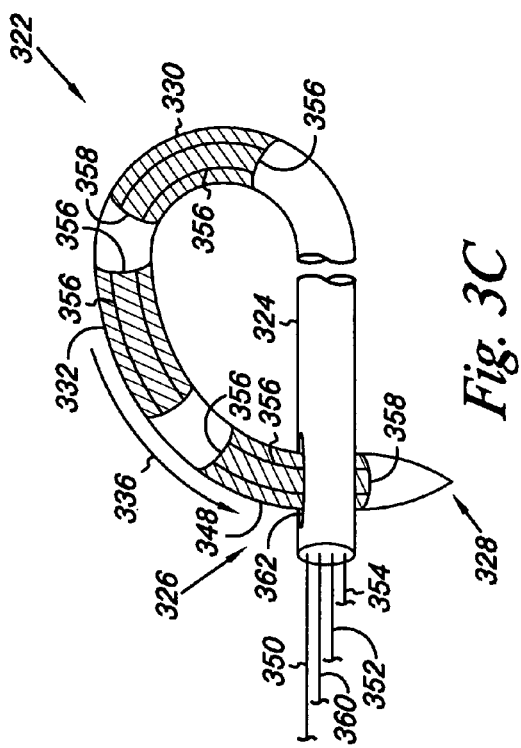

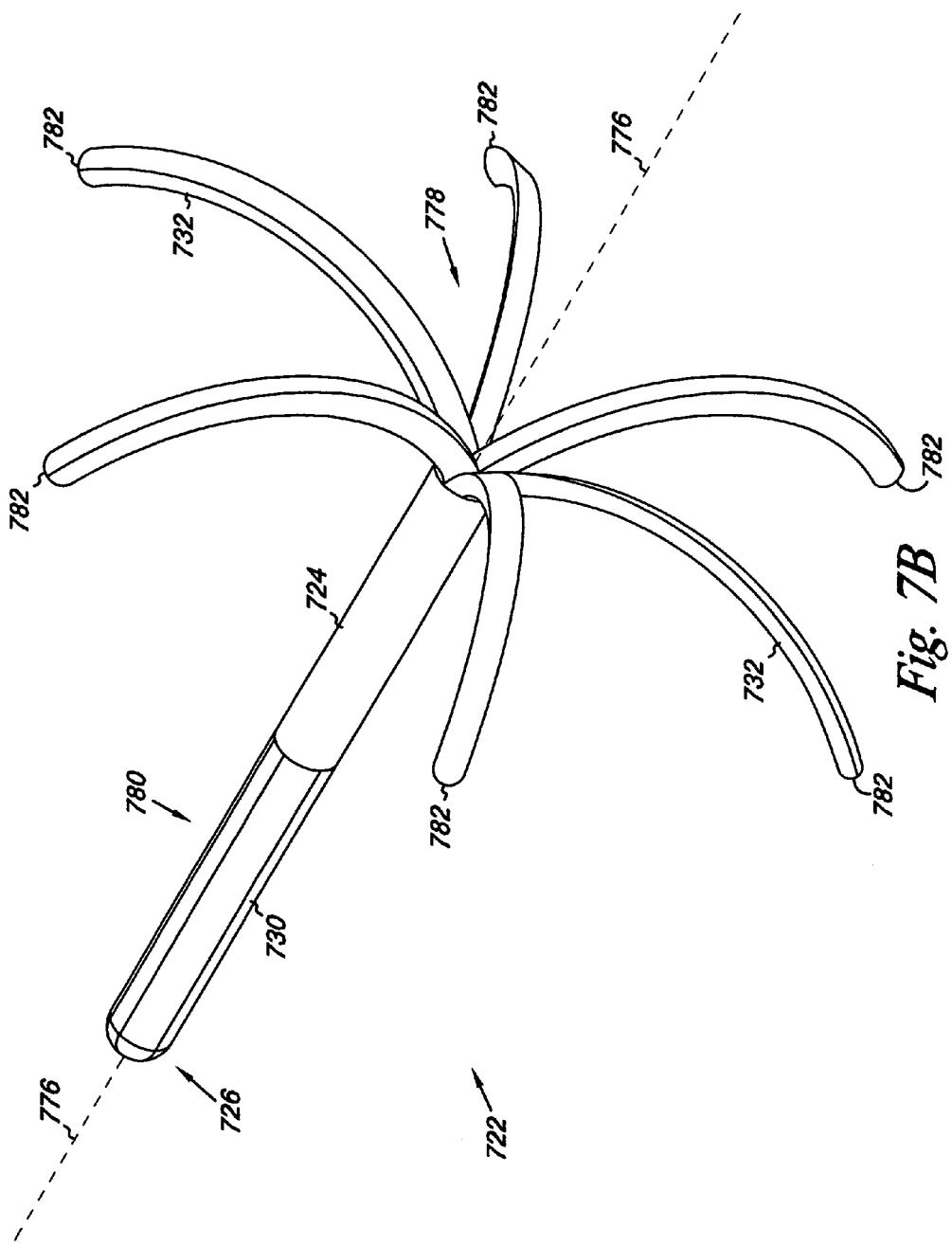

CLOSURE DEVICE, SYSTEM, AND METHOD

TECHNICAL FIELD

The present disclosure relates generally to medical devices and methods for use in cardiac applications; and more particularly to closure devices, system and methods for use with cardiac defects.

BACKGROUND

The human heart is divided into four chambers. They are the right atrium, the right ventricle, the left atrium, and the left ventricle. The right atrium and right ventricle are divided from the left atrium and left ventricle by a wall called the septum. The atrial septum separates the atria, and the ventricular septum separates the ventricles.

Typically, blood flow through the chambers of the heart is directed through the cardiac valves. There exists a cardiac condition, however, in which blood can shunt from one chamber to another through the septum. This is generally referred to as a septal defect.

In the atrial, these septal defects are referred to as atrial septal defects (ASDs). One type of ASD is a patent foramen ovale (PFO). A PFO results when tissues that were used during fetal development to provide a passage (the "foramen ovale") to shut blood from the right atria to the left atria, thereby bypassing the fetal lungs, fail to fuse shortly after birth. As a result, the foramen ovale remains potentially viable, or "patent."

Given the right circumstances, the pressure in the right atrium can exceed that in the left atrium, allowing blood to shunt from the right to the left atrium through the PFO. This would typically be inconsequential, except when the venous blood from the right atrium contains thrombotic debris that would normally travel to the lung to be eliminated by thrombolytic mechanisms. In this case, the thrombotic debris (e.g., a blood clot) can travel to the left atrium where it can potentially cause a myocardial infarction or a stroke.

To close such defects, open surgery may be performed to ligate and close the defect. Such procedures are highly invasive and pose substantial morbidity and mortality risks. Alternatively, catheter based procedures have been developed involving introducing umbrella-like structures into the heart that include opposing expandable structures connected by a hub. One of the expandable structures is inserted through the defect, and both are expanded to secure the tissue surrounding the defect between the structures in an attempt to seal and close the defect. Such structures, however, involve frame structures that support tissues, both of which may fail during the life of the patient being treated, opening the defect, and/or releasing segments of the structure within the patient's heart.

Accordingly, apparatus and methods for closing patent foramen ovale, or other septal defects would be considered useful.

BRIEF DESCRIPTION OF THE DRAWINGS

Structures, elements and the relationship between the structures and elements provided in the figures are not to scale.

FIGS. 2A-2C illustrate an embodiment of a closure device according to the present disclosure.

FIGS. 3A-3C illustrate an embodiment of a closure device according to the present disclosure.

FIGS. 7A-7C illustrate an embodiment of a closure device according to the present disclosure.

DETAILED DESCRIPTION

Figure 1:
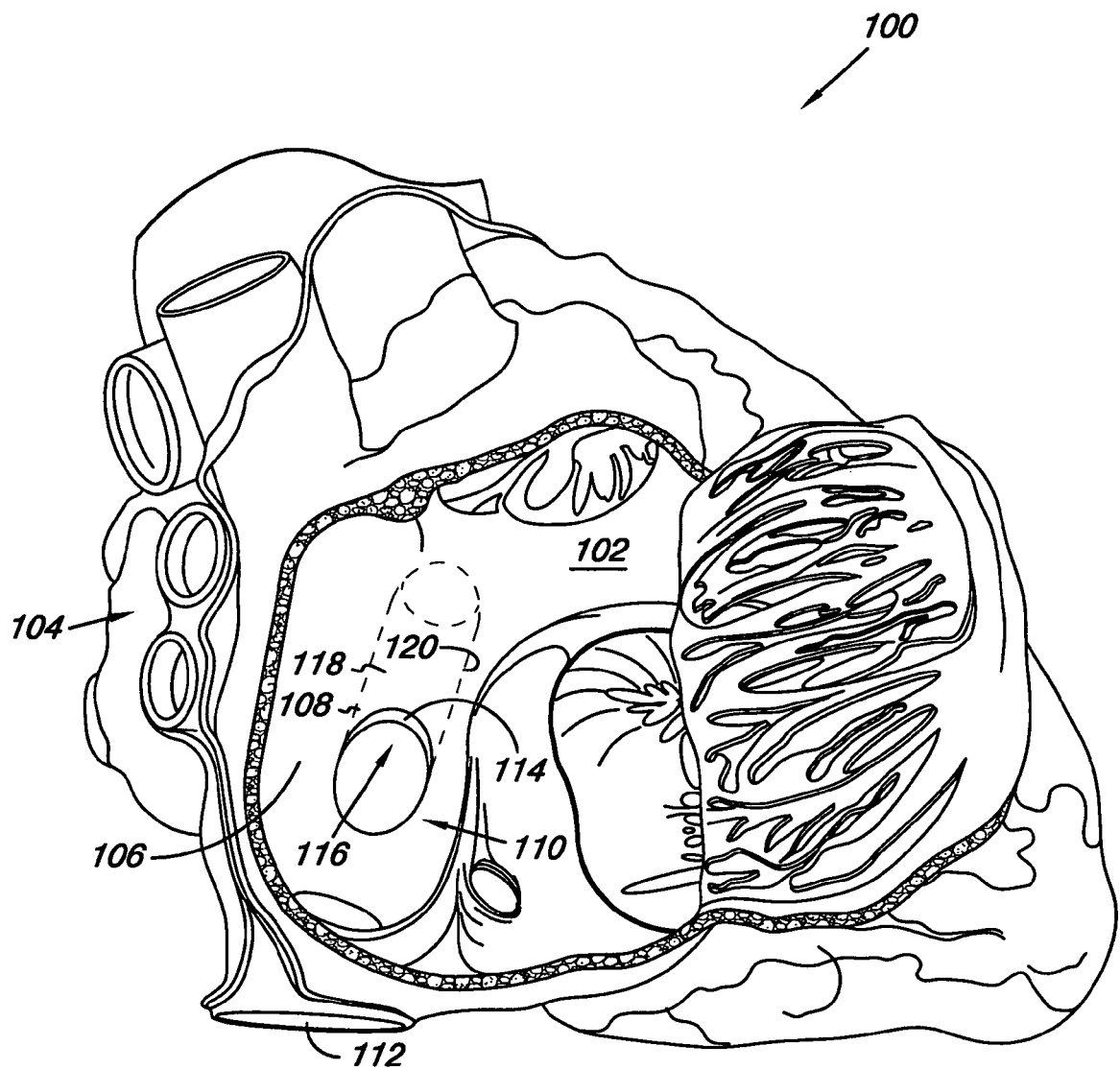
FIG. 1 illustrates a right lateral view of a heart with an opened right atrium.

Embodiments of the present disclosure are directed to closure devices, systems and methods for occluding (e.g., sealing) a septal defect. In one embodiment, the closure devices, systems and methods of the present disclosure can be used in occluding an atrial septal defect, such as a patent foramen ovale (PFO). In addition, the use of two or more of the closure devices of the present disclosure is also possible, where the devices can interact with each other in occluding a PFO. The closure devices, systems and methods of the present disclosure can also be used in occluding other types of septal defects.

Generally, embodiments of the present disclosure provide for an elongate body whose shape can be controlled through the use of an actuator segment associated with the elongate body. As used herein, an "actuator segment" includes a predefined portion on and/or associated with the elongate body that can be controlled through the use of thermal and/or electrical energy supplied to the predefined portion of the elongate body.

In one embodiment, the elongate body according to the present disclosure can be positioned so as to span the tissues (the septum secundum (SS) and the septum primum (SP)) of a PFO. Actuators on the elongate body can then be used to secure the elongate body to the tissues, thereby helping to seal the PFO (e.g., seal the passage defined by the SS and SP). For example, in various embodiments, actuators can be used to control the shape of the elongate body to form a loop around and through the SS and the SP, thereby sealing a PFO. Alternatively, in various embodiments, the actuators can be used to control the shape of the elongate body to radially extend predetermined end portions of the elongate body on either side of the SS and the SP, thereby sealing a PFO. Theses and other embodiments will be discussed more fully herein.

The Figures herein follow a numbering convention in which the first digit or digits correspond to the drawing Figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of the positioning device according to the present disclosure.

FIG. 1 provides an illustration of a right lateral view of a heart 100 with an opened right atrium 102. The heart 100 is divided into four chambers, which are the right atrium 102, a right ventricle, a left atrium 104 and a left ventricle. Heart 100 also includes a septal wall 106 that divides the four chambers of the heart. The portion of the septal wall 106 dividing the right and left atriums 102 and 104 is called the interatrial septum 108. The portion of the septal wall 106 dividing the left and right ventricle is called the ventricular septum.

As illustrated in FIG. 1, the fossa ovalis 110 is situated at the lower part of the interatrial septum 108, above and to the left of the orifice of the inferior vena cava 112. The limbus 114 of the septum secundum (SS) 116 is the pronounced antero-superior margin of the fossa ovalis 110 within the right side (i.e., the right atrium 102) of the interatrial septum 108. It represents the inferior margin of the SS 116 during fetal life.

The passage 118 of the fossa ovalis 110 can be defined by surfaces of the SS (thick tissue) 116 and surfaces of the SP (thin tissue) 120 and extends between the right and left atriums 102 and 104. As used herein, the passage 118 is defined by surfaces of the SS 116 and SP 120 and can be used interchangeably with a PFO. The SS 116 forms the right margin of the passage 118 and comprises the superior portion of the interatrial septum 108. Thus, the SS 116 is located adjacent the limbus 120 and extends upward and rightward away from the limbus 120. The SP 120 forms the left margin of the passage 118 and comprises the inferior portion of the interatrial septum 108 (i.e., below the SS 116) and extends upward and rightward substantially parallel to the SS 116 and toward the left atrium 104.

FIGS. 2A-2C provides an illustration of one embodiment of a closure device 222 according to the present disclosure. As illustrated, closure device 222 includes an elongate body 224 having a proximal end 226 and a distal end 228. In one embodiment, the distal end 228 can be configured as a pointed tip that allows the closure device 222 to pierce the thick tissue (SS) and/or the thin tissue (SP) of, for example, a PFO. The distal end 228 need not, however, be pointed. As will be discussed herein, the closure device 222 can be used in conjunction with a guide catheter and a delivery catheter to pierce the tissues of a septal defect, such as a PFO, and then draw the tissues together thereby sealing the septal defect.

In one embodiment, the closure device 222 includes a first actuator segment 230 and a second actuator segment 232. Each of the first and second actuator segments 230, 232 are associated with the elongate body 224. As discussed herein, the actuator segments 230, 232 include a predefined portion on and/or associated with the elongate body 224 that can be controlled through the use of thermal and/or electrical energy supplied to the predefined portion of the elongate body. For example, the actuator segments 230, 232 can be configured as a layer of a shape memory material, as will be discussed herein, that forms a portion of the elongate body 224. In one embodiment, the layer of the shape memory material forming the actuator segments 230, 232 can extend along the elongate body 224 and completely and/or partially encircle the elongate body 224. In addition, each of the actuator segments 230, 232 can include multiple subdivisions that together form each of the respective actuator segments 230 and/or segments 232. In some embodiments, the closure device 222 can also include more than two actuator segments.

Alternatively, the actuator segments 230, 232 can be configured as a core structure (i.e., a central or innermost part) of the elongate body 224 around which is applied one or more additional materials (e.g., polymers, biomaterials, coatings) in forming the elongate body 224. FIGS. 2A-2C provide an illustration of the actuator segments 230 and 232 having a core structure. Other structures are also possible. For example, in an additional embodiment the actuator segments 230, 232 can be configured as discrete segments that are used (e.g., joined) to form a portion of the elongate body 224. As discussed herein, the actuator segments allow the elongate body 224 to achieve a predefined shape that can function to urge and hold the tissues of a septal defect together, thereby occluding the defect.

FIG. 2A provides an illustration of the closure device 222 in a linear configuration in which the actuator segments 230 and 232 have not yet been activated. As will be discussed herein, a system having a delivery catheter and the closure device 222 can be used in delivering the closure device 222 to seal the septal defect. In one embodiment, the closure device 222 and/or the delivery catheter can be used to pierce the tissues of the septal defect. As will be appreciated, the closure device 222 in its linear configuration can be sufficiently rigid (e.g., has sufficient column strength) to allow the elongate body 224 to pierce the tissues of a septal defect, such as a PFO. In one embodiment, once the device 222 has pierced the tissue of the septal defect the distal end 228 and the proximal end 226 are on opposite sides of the septal defect tissues.

FIG. 2B provides an illustration in which the first actuator segment 230 allows the elongate body 224 to bend to a first predetermined position 234. As illustrated, the distal end 228 extends towards the proximal end 226 when the elongate body is in the first predetermined position 234. In other works, the distal end 228 is located closer to the proximal end 226 of the elongate body 224 in the first predetermined position as compared to its unbent configuration illustrated in FIG. 2A. In the present embodiment, the first actuator segment can position the distal end 228 and the second actuator segment 232 at an angle relative the proximal end 226 and the adjacent elongate body 224 from about 135 degrees to 225 degrees. In other words, the first actuator segment 230 can reposition the distal end 228 from about 135 degrees to 225 degrees relative its original position as illustrated in FIG. 2A. As illustrated in FIG. 2B the first actuator segment positions the distal end 228 and the second actuator segment 232 at an angle of 180 degrees relative the original position of the distal end 228 illustrated in FIG. 2A.

In one embodiment, once the elongate body 224 is in the first predetermined position 234 the closure device 222 can then be pulled back across the tissues of the septal defect using, for example, the delivery catheter. Once pulled through the tissues of the septal defect, both the proximal end 226 and the distal end 228 of the elongate body 224 are on the same side of the septal defect. In an alternative embodiment, the motion of elongate body 224 moving toward the first predetermined position 234 can allow the distal end 228 to pass back through the tissues of the septal defect. In other words, the elongate body 224 need not be moved (i.e., pulled) by the operator to bring the closure device 222 back across the tissues of the septal defect.

FIG. 2C provides an illustration of where the second actuator segment 232 allows the elongate body 224 to bend to a second predetermined position 236 so that the distal end 228 and the proximal end 226 are more closely positioned than when in the first predetermined position 234, as shown in FIG. 2B. As illustrated, the distal end 228 can be positioned either adjacent to or in contact with a portion of the elongate body 224 that is adjacent the proximal end 226 of the elongate body 224. In one embodiment, the elongate body 224 can be held in this loop configuration illustrated in FIG. 2C with the distal end 228 abutting the elongate body 224. Alternatively, the second actuator segment 232 can be used to wrap at least a portion of the elongate body 224 adjacent the distal end 228 around a portion of the elongate body 224 adjacent the proximal end 226. In additional embodiment, the elongate body can defines a longitudinal slit adjacent the proximal end to receive the distal end of the elongate body when in the second predetermined position, as will be discussed and illustrated herein.

In one embodiment, once the second actuator segment 232 allows the elongate body 224 to bend to its second predetermined position 236, the closure device 222 helps to prevent the tissues of the septal defect from moving away from each other, and thus, fasten the tissues. For example, the various embodiments of the closure device described herein may be used to occlude a patent foramen ovale. As used herein, "occlude" refers to causing a body passage to become closed or at least partially closed, or preventing the passage of blood and/or particles in the blood through a body passage. For example, embodiments of the present disclosure can include devices, systems and methods to pierce tissue of the septum secundum (SS) and the septum primum (SP) and to occlude the passage of a patent foramen ovale (PFO) defined by the tissue of the SS and the SP.

As will be appreciated, the closure device 222 can be configured to allow the elongate body 224 to be positioned next to and/or press against the tissues of the septal defect when the first and second predetermined positions 234, 236 have been achieved. As illustrated, the elongate body 224 can have a loop configuration that can help to draw the tissues of a septal defect more closely together. Alternatively, the elongate body 224 can have a more rectilinear configuration after bending to the first and second predetermined positions 234, 236 to allow for contact with the tissues. Other shapes are possible.

In one embodiment, the first and second actuator segments 230, 232 can be used to either bend (e.g., move) the elongate body 224 and/or allow the elongate body 224 to return to a predetermined shape. For this later situation, the elongate body 224 can be formed with the first and second predetermined positions 234, 236. By way of example, the elongate body 224 for this embodiment would look similar to that shown in FIG. 2C. The first and second actuator segments 230, 232 can then be used to restrain, or hold, the elongate body 224 from bending towards the first and second predetermined position 234, 236. When activated, the first and second actuator segments 230, 232 would relax so as to allow the elongate body 224 to return towards its predetermined shape. In other words, the actuator segments 230, 232 in this embodiment function to hold the elongate body 224 in a state of stress when in the straight configuration (e.g., FIG. 2A) until such time as the segments 230, 232 are activated thereby allowing the elongate body 224 to bend back to its predetermined shape.

The first and second actuator segments 230, 232 can also be used to bend (e.g., move) the elongate body 224. For example, the elongate body 224 can have a straight configuration (e.g., FIG. 2A) in a relaxed unstressed state. Each of the first and second actuator segments 230, 232 can then be activated so as to bend the elongate body 224 into the predetermined positions. In other words, the first and second actuator segments 230, 232 are responsible for moving the elongate body 224.

In one embodiment, each of the first and second actuator segments 230, 232 are separated from each other along the elongate body 224. Alternatively, the actuator segments 230, 232 could abut each other. In addition, each of the first and second actuator segments 230, 232 can function, as discussed herein, independently of each other. So, the first actuator segment 230 can be activated without activating the second actuator segment 232 and visa versa. In an additional embodiment, more than two actuator segments can be used with the elongate body. For example, the elongate body 224 could further include a third actuator segment, or more, that can function as described for the first and second actuator segments 230, 232.

In one embodiment, the shape memory material useful for the actuator segments described herein includes, besides other materials, a shape memory polymer. Shape memory polymers (SMPs) are typically have formulations based on styrene acrylate, cyanate ester, and epoxy polymer systems. In addition, block and segmented copolymers suitable for use as a SMP include polyetherurethanes, polyesterurethanes, poyetherpolyesters, polyetherpolyamides, and others with polyether or polyester soft segments.

Using an SMP allows the predetermined shape as discussed herein to be imparted, or to be "memorized", in forming the actuator segment. The SMP can then change between a rigid and an elastic state by way of thermal stimuli, in other words application of heat. The change takes place at what is referred to as the glass transition temperature ($T_g$). SMP can be formulated with a $T_g$ that matches an application need. In the present disclosure, $T_g$ for a suitable SMP can be in a range of 40° C. to 80° C. Above its transition temperature, which can be custom-engineered, SMP goes from a rigid, plastic state to a flexible, elastic state. When cooled below that temperature, it becomes rigid again, with high specific strength. When heated above its transition temperature, the SMP returns to its "memorized" shape.

In an alternative embodiment, the shape memory material useful for the actuator segments described herein can also include an electroactive polymer (EAP). EAPs are polymers whose shape is modified when an electrical current is applied to them. EAPs can undergo deformation while sustaining large forces. Suitable EAPs can include dielectric EAPs and ionic EAPs. For example, a suitable EAP can be polypyrole.

Referring again to FIG. 2A-2C, the elongate body 224 includes a first conductive element 240 and a second conductive element 242 that extend from the proximal end 226 to the first actuator segment 230 and the second actuator segment 232, respectively. In the present embodiment, the first and/or second actuator segments 230, 232 can be a SMP, where the first and second conductive elements 240, 242 provide thermal energy (i.e., heat) to the SMP of the first and second actuator segments 230, 232. In one embodiment, the first and second conductive elements 240, 242 include a resistive heating element 244 and 246 positioned adjacent to and/or within the SMP of the first and second actuator segments 230, 232, respectively. For example, the individual resistive heating element 244 and 246 can span the length of the respective first and second actuator segments 230, 232. Alternatively, the individual resistive heating element 244 and 246 can be positioned adjacent the respective first and second actuator segments 230, 232 at one or more predetermined locations. The resistive heating element 244 and 246 can also be configured to heat preferentially from one end towards the opposite end of the respective first and second actuator segments 230, 232.

In one embodiment, the conductive elements can be formed of conductive metal and/or metal alloys such as gold, titanium, medical grade stainless steel (e.g., 316L), titanium, tantalum, platinum alloys, niobium alloys, cobalt alloys, alginate, MP35N, aluminum alloys, chromium alloys, vanadium alloys, memory alloys, or combinations thereof. In addition, the elongate body 224 can be formed from medical grade polymers and/or co-polymers, such as polypropylene, polystyrene, polyurethane, polyvinylchloride, polyethylene, polyetheretherketone, polyetherimide, polyamides, polycarbonate, biodegradables and combinations thereof. Other medical grade polymers, metals, and metal alloys for the above applications are also possible.

FIG. 3A-3C provides an additional embodiment of the closure device 322 according to the present disclosure. As illustrated, the closure device 322 includes the elongate body 324 having proximal end 326 and distal end 328. The closure device 322 further includes the first actuator segment 330, the second actuator segment 332 and a third actuator segment 348. Each of the first, second and third actuator segments 330, 332, and 348 are associated with the elongate body 324. In addition, in some embodiments, the closure device 322 can include more than three actuator segments.

As discussed, the actuator segments 330, 332, 348 could be provided as a layer that at least partially encircles the elongate body 324, a core structure of the elongate body 324 and/or as a discrete segment or section that forms a complete portion of the elongate body 324. In the present embodiment, the actuator segments 330, 332, 348 are provided as a layer that at least partially encircles the elongate body 324. In addition, the first, second and third actuator segments 330, 332, and 348 can be used to either bend (e.g., move) the elongate body 324 and/or allow the elongate body 324 to return to the predetermined shapes, as discussed herein.

In one embodiment, one or more of the first, second and third actuator segments 330, 332, and 348 can be formed from, besides other materials, an EAP, as discussed herein. In addition to forming the actuators from an EAP, the elongate body 324 can include a first lead 350, a second lead 352 and a third lead 354 that extend from the proximal end 326 to the first, second and third actuator segment 330, 332, and 348, respectively. The leads 350, 352 and 354 can be used to supply electrical current to the EAP of the first, second and third actuator segments 330, 332, and 348.

In one embodiment, the leads 350, 352 and 354 can each be coupled to an electrode 356 (e.g., a cathode) that can be used to supply the electrical current to the EAP of each of the first, second and third actuator segments 330, 332, and 348. A second electrode 358 (e.g., an anode) can either be positioned on either the surface of the elongate body 324 and/or the delivery catheter used with the delivery device 322. As will be appreciated, the electrode polarity could be reversed.

As illustrated in FIGS. 3A-3C, each electrode 356 can be positioned adjacent its respective first, second and third actuator segment 330, 332, and 348. In one embodiment, the electrode 356 can be positioned adjacent its respective actuator segment to allow electrical current to pass through the EAP of the segment to the second electrode 358. In one embodiment, the electrode 356 can be configured to provide a sufficiently large surface area to maintain a reasonable current density through the EAP. In one embodiment, each electrode 356 can be associated with and control an individual actuator segment 330, 332, and 348.

In one embodiment, the electrode 356 could be a ring, or partial ring, electrode positioned beneath and/or adjacent each of the actuator segments 330, 332, and 348. In the ring or partial ring configuration, the electrode 356 will be sufficiently flexible to allow for the actuator segments 330, 332, and 348 and/or the elongate body 324 to bend to the predetermined shapes, as discussed herein. For example, the electrode 356 could be a conductive film of a metal and/or metal alloy (e.g., gold, titanium, medical grade stainless steel (e.g., 316L), titanium, tantalum, platinum alloys, niobium alloys, cobalt alloys, alginate, MP35N, aluminum alloys, chromium alloys, vanadium alloys, or combinations thereof) positioned at least partially between the elongate body 324 and the respective actuator segments 330, 332, and 348.

In an additional embodiment, the electrode 356 could be configured in an array or a series of conductors (e.g., wires) that extend through and/or adjacent to the actuator segments 330, 332, and 348. In an alternative embodiment, the array or series of conductors could extend in a helical fashion along the elongate body 324. Alternatively, the array or series of conductors could extend in a linear fashion along the elongate body 324.

As discussed, the second electrode 358 (e.g., an anode) can be positioned on the surface of the elongate body 324. In one embodiment, at least one surface of the second electrode 358 is exposed to the environment surrounding the elongate body 324. The second electrode 358 can have a number of different predetermined shapes. For example, the second electrode 358 can be configured as an annular and/or a semi-annular ring. Use of other shapes is possible. Embodiments of the present disclosure are not limited to two electrodes. In addition, the electrodes can be part of a separate system from the closure device 322 and/or elongate body 324.

In one embodiment, one or more of the second electrode 358 can be used with the closure device 322. For example, one of the second electrodes 358 could be use as the anode for each of the electrodes 356 couple to the leads 350, 352 and 354. In other words, one of the second electrodes 358 is used as common electrode for providing electrical current through each individual electrode 356 of leads 350, 352 and 354. In an alternative embodiment, more than one of the second electrodes 358 can be used with the elongate body 324. For example, three of the second electrodes 358 could be used with the elongate body 324 as illustrated in FIG. 3A-3C, where the second electrode 358 is positioned adjacent the actuator segments 330, 332, and 348. Each of the three second electrodes 358 could be connected to an individual lead. Alternatively, the three second electrodes 358 could be connected in common with a single common lead 360.

As illustrated, a combination of the actuator segments 330, 332 and 348 can be used to bend, or cause to bend, the elongate body 324. For example, a combination of the first and second actuator segments 330 and 332 can be used to bend the elongate body 324 to the first predetermined position 334. As illustrated, the distal end 328 extends towards the proximal end 326 when the elongate body is in the first predetermined position 334. In the present embodiment, the first and second actuator segments 330 and 332 can position the distal end 328 and the second actuator segment 332 at an angle relative the proximal end 326 and the adjacent elongate body 324 from about 135 degree to 225 degree.

In an additional embodiment, the third actuator segment 356 allows the elongate body 324 to bend to a second predetermined position 336 in which the distal end 228 and the proximal end 226 are more closely positioned than when in the first predetermined position 334. As illustrated, the distal end 328 can be positioned either adjacent to or in contact with a portion of the elongate body 324 that is adjacent the proximal end 326 of the elongate body 324. As will be appreciated, each of the actuator segments 330, 332 and 356 can be used to bend the elongate body 324 to three individual predetermined positions (e.g., a first, second, and third predetermined position, respectively).

In one embodiment, the elongate body 324 can be held in this loop configuration illustrated in FIG. 3C with the distal end 328 abutting the elongate body 324. For example, in the present embodiment, the elongate body 324 defines a longitudinal slit 362, or opening, adjacent the proximal end 326 to receive the distal end 328 of the elongate body 324 when in the second predetermined position 336. In one embodiment, the distal end 328 can slide into the longitudinal slit 362 from the compressive force supplied by the second actuator segment 332. Alternatively, the perimeter of the slit 362 can include an SMP or an EAP that can be used to open the slit 362 sufficiently to receive the distal end 328 of the elongate body 324.

Figure 4:
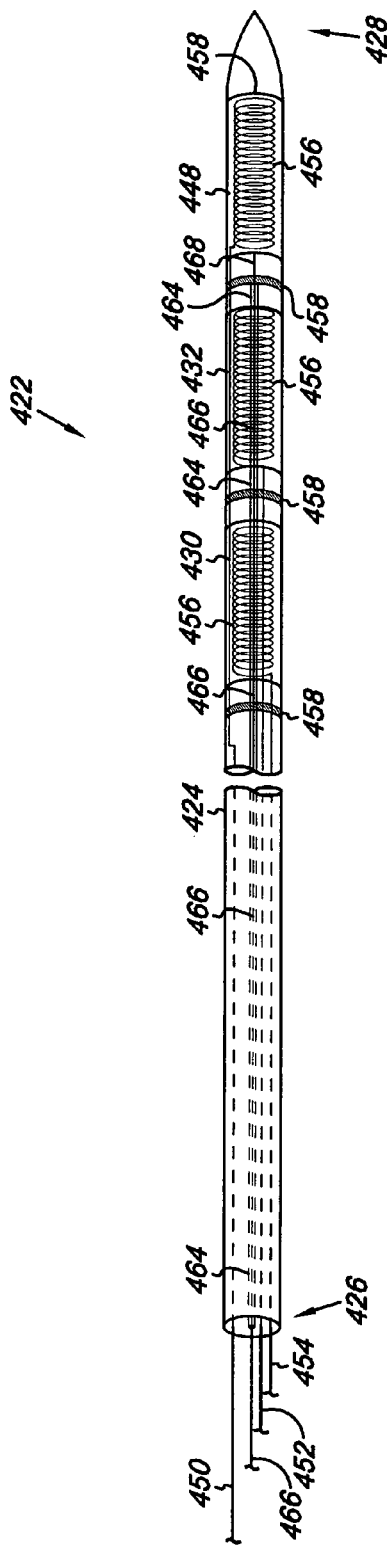
FIG. 4 illustrates an embodiment of a closure device according to the present disclosure.

FIG. 4 provides an additional embodiment of the closure device 422 according to the present disclosure. As illustrated, the closure device 422 includes the elongate body 424 with proximal end 426, distal end 428, and the first, second and third actuator segment 430, 432 and 448. The closure device 422 further includes leads 450, 452 and 454 each coupled to electrode 456 (e.g., a cathode), as discussed herein, that can be used to supply electrical current to the EAP of each of the first, second and third actuator segments 430, 432, and 448.

As illustrated, the elongate body 424 can further include a lumen 464 extending from the proximal end 426 to at least the first, second, and third actuator segments 430, 432, and 448. In one embodiment, the lumen 464 can be centric or eccentrically positioned in the elongate body 428. The lumen 464 can have a circumference sufficiently large enough to receive and pass a positionable lead 466. In one embodiment, the positionable lead 464 extends through and can be moved within the lumen 462 to allow electrical current to be conducted through the EAP of the first, second, and third actuator segments 430, 432, and 448 using electrode 456.

In one embodiment, the positionable lead 466 can be formed of an electrically conductive material (e.g., metal or metal alloy) with or without an insulating sheath. The positionable lead 466 can further include a distal end 468 configured to make positive physical contact with the surface defining the lumen 464. For example, the positionable lead 466 can have a predetermined bend or deflection adjacent the distal end 468 to allow for contact with the surface of the lumen 464.

In one embodiment, the second electrode 458 includes at least one portion surface that defines the lumen 464. The positionable lead 466 can be moved within the lumen 464 to allow at least the distal end 468 and/or a portion of the lead 466 adjacent the end 468 make contact with the portion of the second electrode 458 helping to define the lumen 464. As illustrated, the second electrode 458 also defines a portion of the exterior surface of the elongate body 424.

In one embodiment, the positionable lead 466 can be moved through the lumen 464 allowing for isolated electrical contact to be made with each of the second electrodes 458 associated with the elongate body 428. In one embodiment, the surface of the second electrode 458 defining a portion of the lumen 462 surface can include a notch into which the lead 466 can releasably seat. In one embodiment, marks on the positionable lead 466 adjacent the proximal end can be used allow the user to identify which of the second electrode 458 is in electrical contact with the positionable lead 466.

In one embodiment, the positionable lead 466 can be moved within the lumen 464 to make electrical contact with the desired second electrode 458. Electrical current can then be applied across one or more of the first, second, and third actuator segments 430, 432, and 448 using the appropriate second electrode 458 and the electrode 456, as discussed herein, to cause the device 422 to bend to the first and second predetermined positions.

Figure 5A:
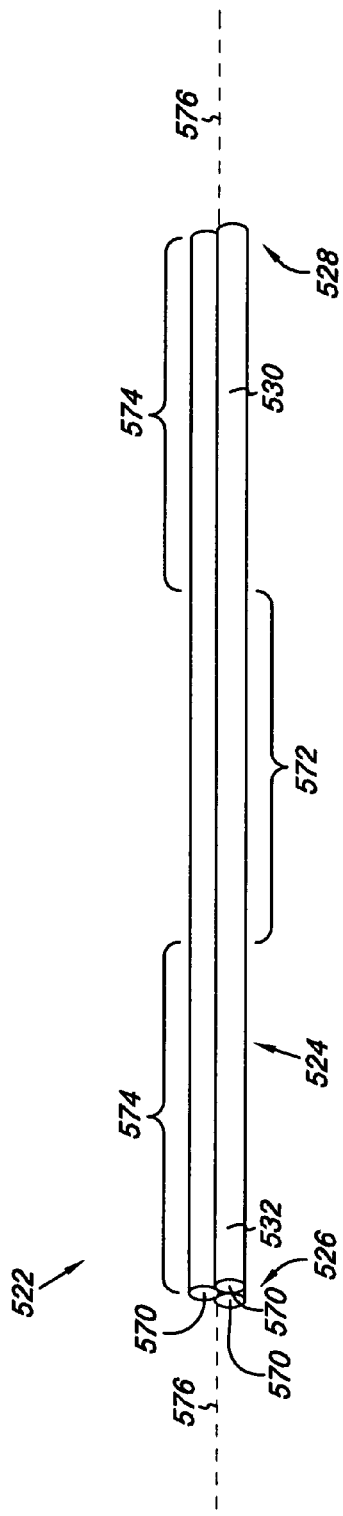
FIGS. 5A-5C illustrate an embodiment of a closure device according to the present disclosure.
Figure 5B:
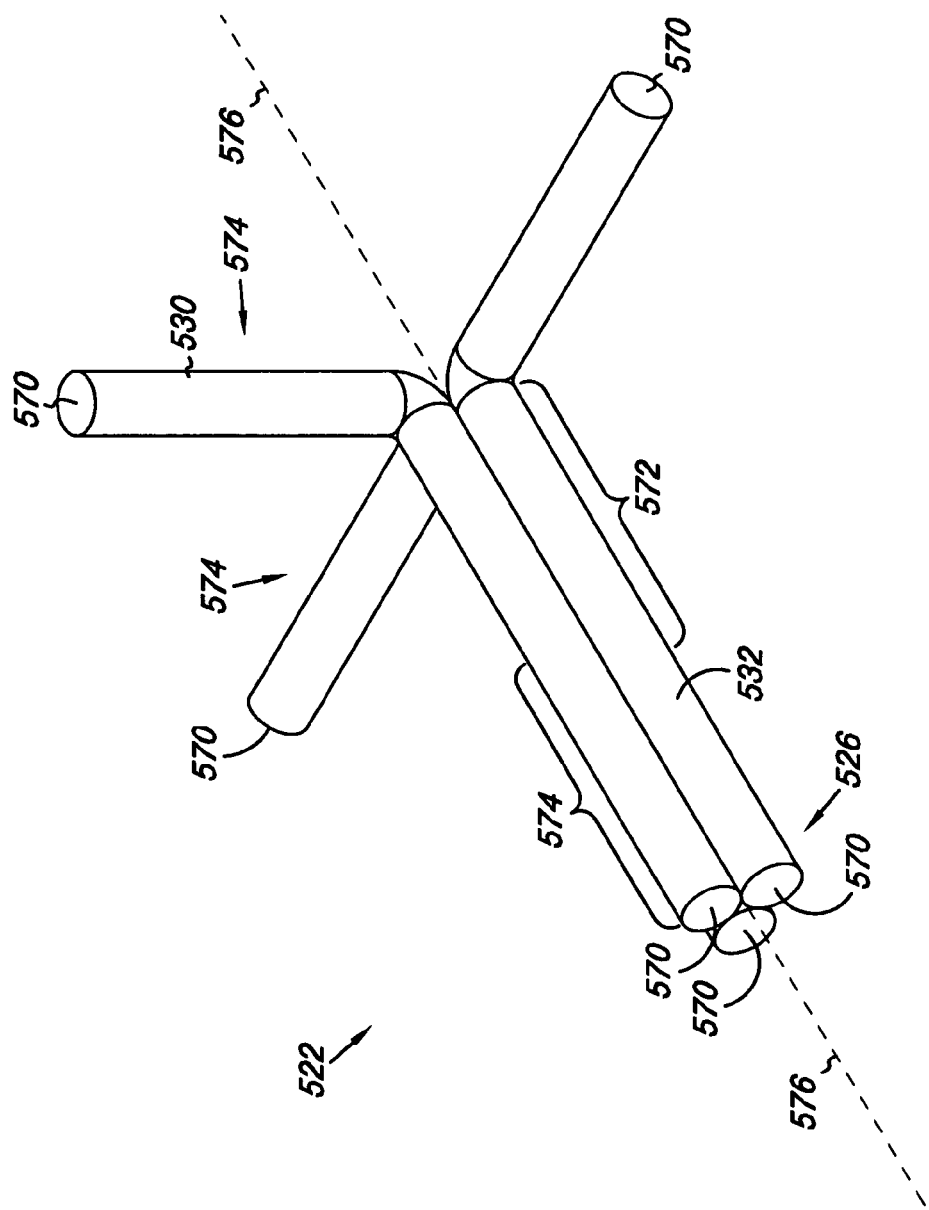
Figure 5C:
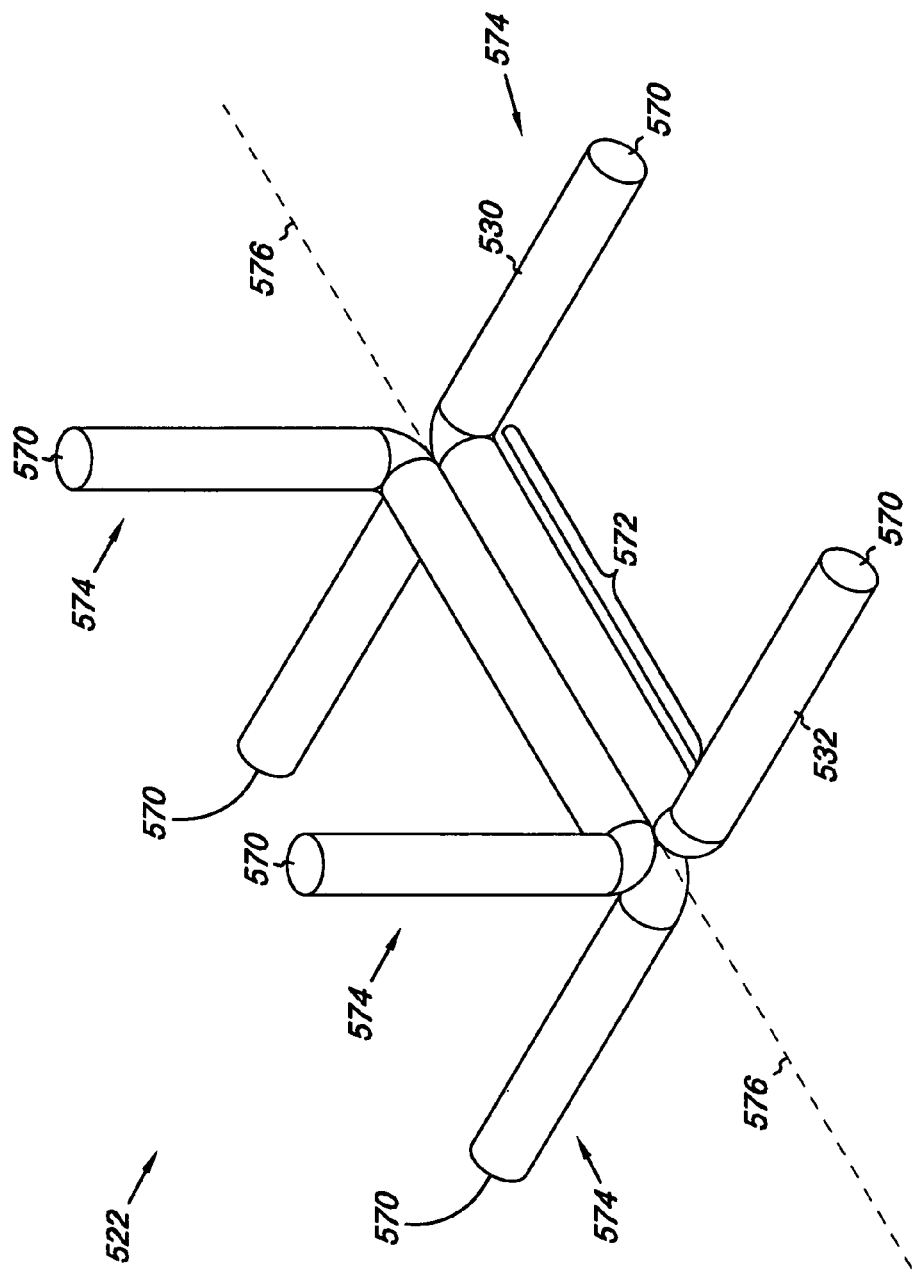

FIGS. 5A-5C provide an additional embodiment of the closure device 522 of the present disclosure. In one embodiment, the closure device 522 has an elongate body 524 that includes two or more wires 570. The wires 570 can be bundled together along a central portion 572 of the elongate body 524. Bundling the wires 570 can include twisting the wires 570 together. Alternatively, bundling the wires 570 can include weaving and/or braiding the wires 570 together to provide the central portion 572 of the elongate body 524. The wires 570 could also be straight, as illustrated. In addition, the wires 570 in the central portion 572 can be fused together (e.g., laser welded).

The closure device 522 further includes a first actuator segment 530 and a second actuator segment 532. In one embodiment, the first actuator segment 530 and the second actuator segment 532 can be formed by a predetermined portion 574 of one or more of the wires 570 extending from the central portion 572 of the elongate body 524. The first and second actuator segments 530, 532 allow for the predetermined portion 574 of each of the two or more wires 570 to extend radially from a common axis 576 running through the central portion 572 of the elongate body 524. So, for example, the first actuator segment 530 allows the predetermined portion 574 of each of the two or more wires 570 adjacent the distal end 528 to extend radially from the common axis 576. Similarly, the second actuator segment 532 allows the predetermined portion 574 of each of the two or more wires 570 adjacent the proximal end 526 to extend radially from the common axis 574. FIGS. 5B and 5C provide illustrations of these embodiments.

In use, the distal end 528 of the closure device 522 can first be inserted across the tissues of the septal defect so that the proximal end 526 and the distal end 528 are on opposite sides of the septal defect. The first actuator segment 530 can then be used to cause the predetermined portion 574 of the wires 570 adjacent the distal end 528 to flare radially. In a similar fashion, the second actuator segment 532 can then be used to cause the predetermined portion 574 of the wires 570 adjacent the proximal end 526 to flare radially. As the predetermined portion 574 of the wires 570 flare radially, they contact and draw the tissue of the septal defect more closely together, thereby helping to seal the septal defect.

In one embodiment, the predetermined portion 572 forming the first actuator segment 530 and the second actuator segment 532 can be a coating of either the SMP and/or EMP, as discussed herein, on the wire 570. Alternatively, the predetermined portion 574 forming the first actuator segment 530 and the second actuator segment 532 can be a core of either the SMP and/or EMP, as discussed herein, which is coated with an electrically conductive material.

In one embodiment, the wires 570 themselves can be used as electrodes to provide either the thermal energy (i.e., heat) and/or the electrical current to cause the predetermined portion 574 of the actuator segments 530, 532 to extend radially from the common axis, as illustrated in FIGS. 5B-5C. In one embodiment, the wires 570 forming the predetermined portion 574 of the first and second actuator segments 530, 532 can be positioned adjacent each other. A first predetermined group of the wires 570 (e.g., one or more) can be used as a first electrode (e.g., the cathode), while a second predetermined group of the wires 570 can be used as the second electrode (e.g., the anode). When the actuator segments 530 and 532 include a coating of EMP, electrical current can flow between the wires 570 forming the electrodes allowing for the EMP to change shape. Alternatively, when the actuator segments 530 and 532 include a coating of SMP, the wires 570 can form a conductive loop through which current can be passed to heat the SMP so as to cause the wires 570 to change shape, as discussed herein.

Alternatively, the wires 570 can be used as the first electrode (either anode or cathode), while the second electrode can be provided at a site distal from the wires 570. For example, the opposite electrode could be temporarily provided on the skin of the patient (e.g., mounted cutaneously and/or subcutaneously).

In an additional embodiment, separate conductive elements (e.g., an insulated wire) can extend through the elongate body 524 to a resistive heating element positioned adjacent to and/or within the actuator segment 530 or 532 formed with a core or coating of SMP. Alternatively, separate leads can extend through the elongate body 524 to provide a first electrode (e.g., a cathode) positioned adjacent to and/or within the actuator segment 530 or 532 formed with a core or coating of EMP, where the second electrode (e.g., an anode) could be located away from the closure device 522. Alternatively, the actuator segments 530 and 532 could act as the first and second electrodes in providing electrical current through the EMP. Other configurations are also possible.

In an alternative embodiment, the wires 570 could be formed of a memory material, such as a shape memory polymer and/or from a shape memory metal in which has the first and second predetermined positions are set. The closure device 522 could then be elastically deformed into a configuration for delivery, where upon during deployment the memory material forming the wires causes the device 522 to move towards the predetermined positions. Alternatively, heating elements, as discussed herein, could be used to heat a memory metal to a transition temperature, thereby allowing for movement in the actuator segments 530, 532. Examples of shape memory metals include, but are not limited to, and memory metals alloys such as Nitinol, titanium-palladuim-nickel, nickel-titanium-copper, gold-cadmium, iron-zinc-copper-aluminum, titanium-niobium-aluminum, hafnium-titanium-nickel, iron-manganese-silicon, nickel-titanium, nickel-iron-zinc-aluminum, copper-aluminum-iron, titanium-niobium, zirconium-copper-zinc, and nickel-zirconium-titanium. Other metal and metal alloys are also possible.

Figure 6A:
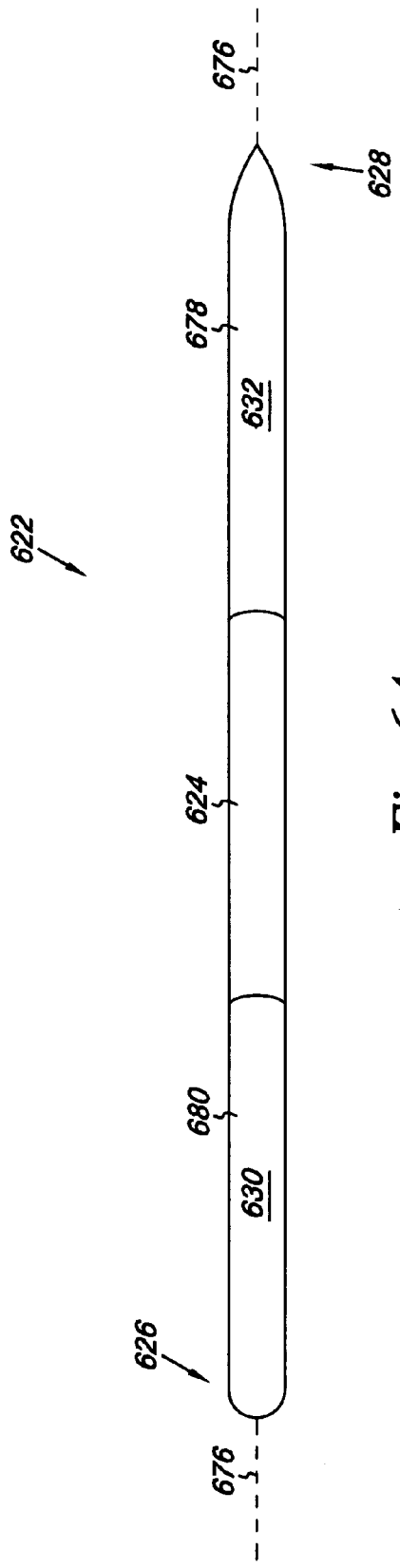
FIGS. 6A-6C illustrate an embodiment of a closure device according to the present disclosure.
Figure 6B:
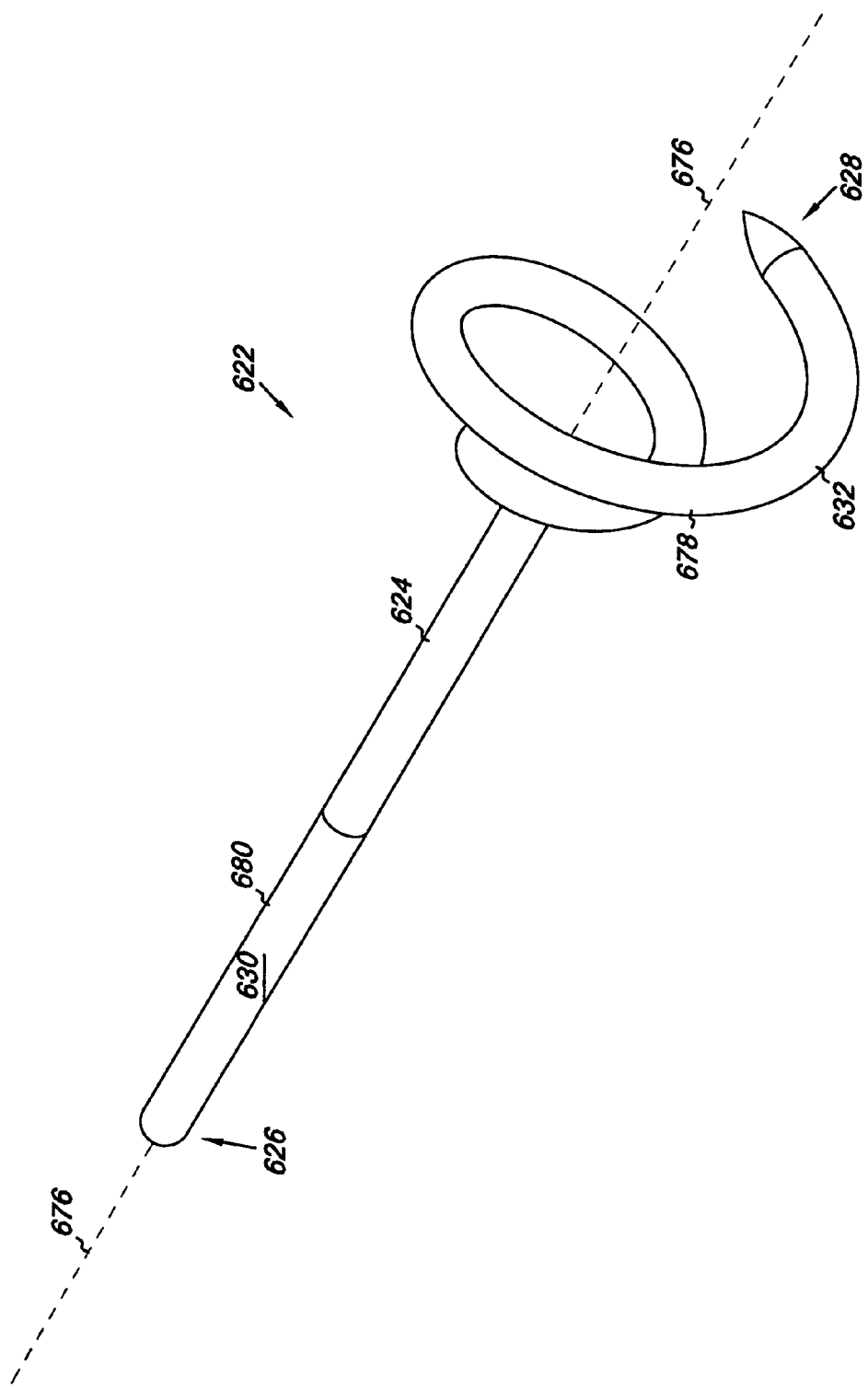
Figure 6C:
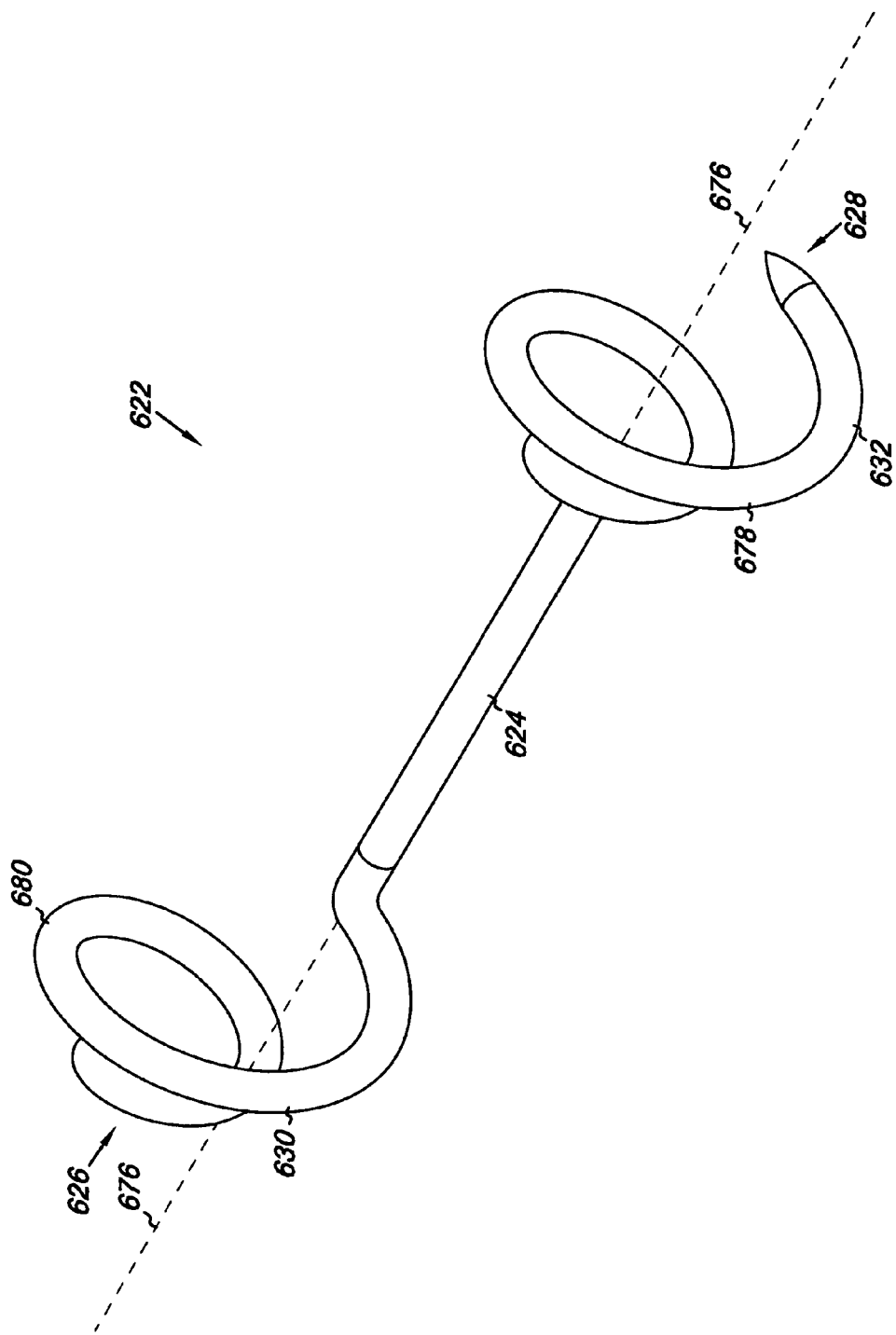

FIG. 6A-6C provide an additional embodiment of the closure device 622 according to the present disclosure. In one embodiment, the closure device 622 has an elongate body 624 that includes a first actuator segment 630 and a second actuator segment 632. The first and second actuator segments 630, 632, including the leads and/or connections, can be formed as discussed herein.

In one embodiment, the first and second actuator segments 630, 632 are configured to allow a first predetermined section 678 of the elongate body 624 adjacent the distal end 628 and a second predetermined section 680 of the elongate body 624 adjacent the proximal end 626 to extend radially from the common axis 676. The first and second predetermined sections 678, 680 can extend in a concentric 682 and/or eccentric 684 fashion from and/or around the common axis 676, as illustrated in FIG. 6C.

In one embodiment, the shape of the predetermined sections 678, 680 allows the closure device 622 when positioned across the tissues of a septal defect to hold the tissues of the septal defect together so as to occlude the defect. In the present embodiment, the predetermined sections 678, 680 allow the elongate body 624 to bend into a spiral shape. In addition, the predetermined sections 678, 680 can extend radially in a common plane or can be non-planar. Examples of a non-planar configuration include conical, semi-spherical, or other non-planar geometric configuration.

Other shapes for the predetermined sections 678, 680 of the elongate body 624 are also possible. For example, other shapes can include those have a polygonal configuration, helical shapes, vortex shapes, crescent shapes, curved shapes, saddle shapes, and irregular shapes. In various embodiments, these predefined shapes can include surfaces and structures that help to engage the tissues of the septal defect. As used herein, engaging the tissue of a septal defect can include piercing, trapping, squeezing, clamping, grasping, gripping, hooking, abutting, catching, and pushing the tissues of the passage to fasten the tissue and occlude the septal defect.

Figure 7A:
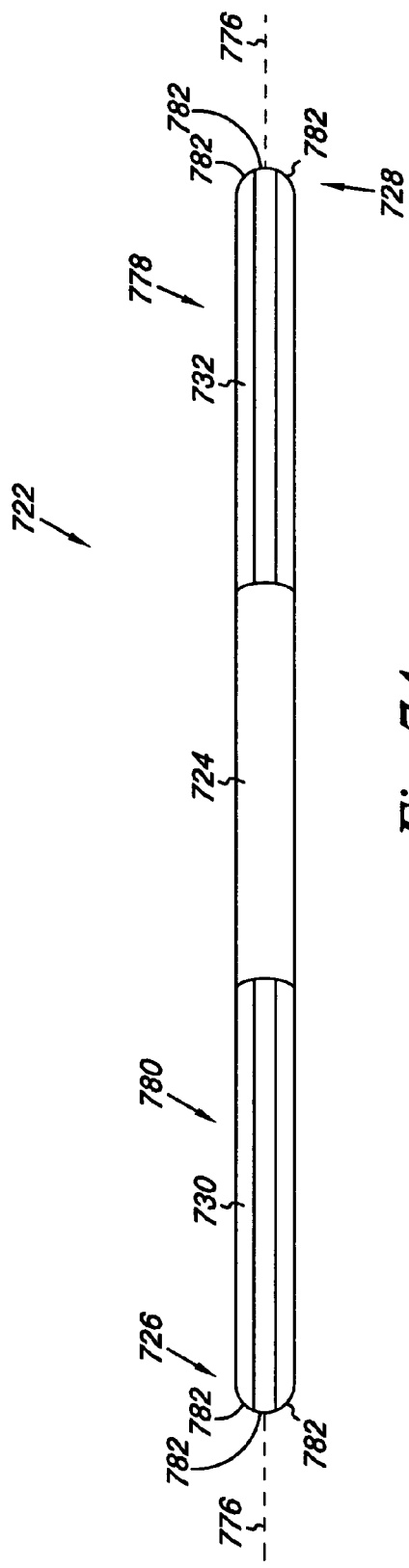
Figure 7C:
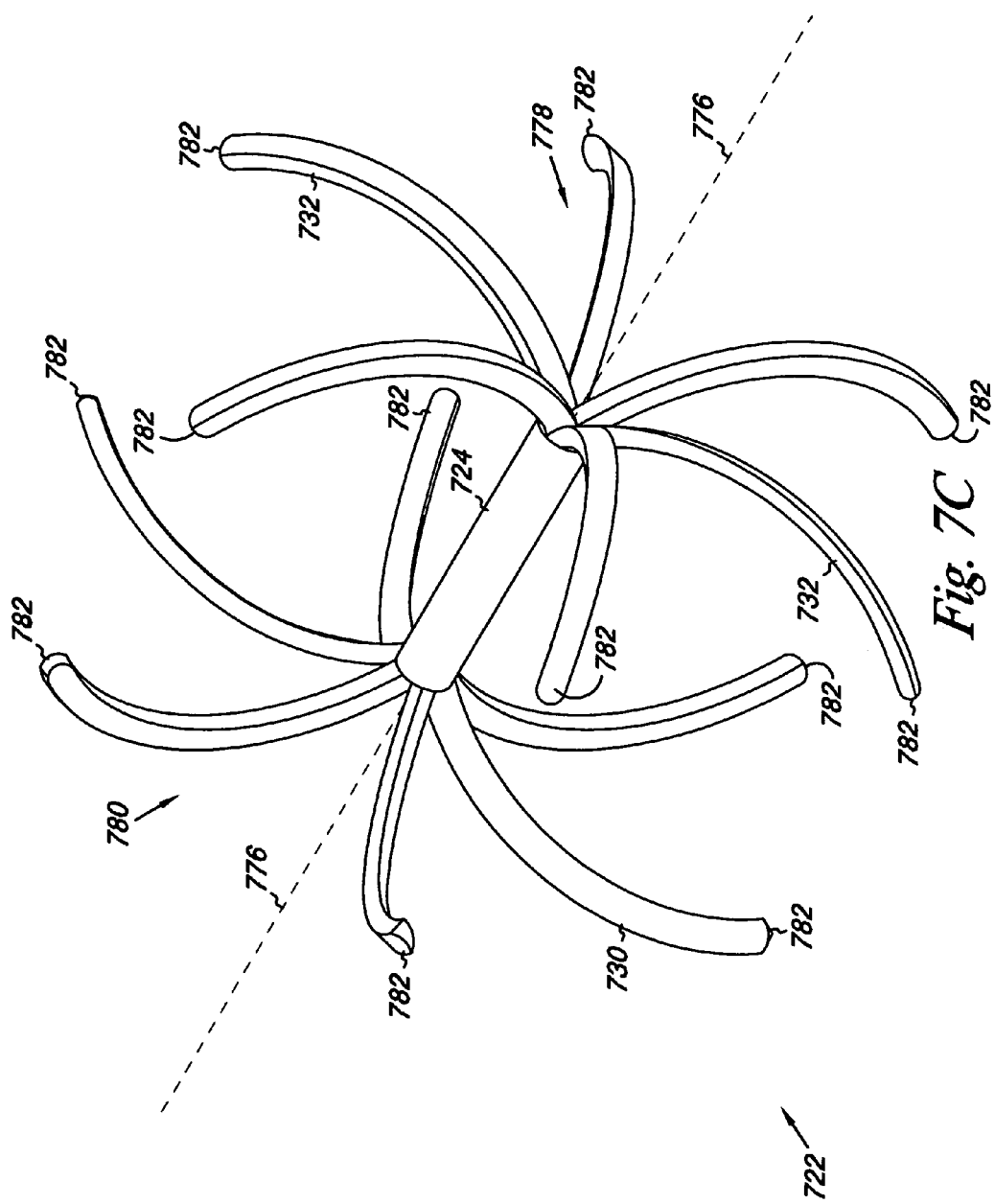

FIGS. 7A-7C provide an additional embodiment of the closure device 722 according to the present disclosure. In one embodiment, the closure device 722 has an elongate body 724 that includes a first actuator segment 730 and a second actuator segment 732. The first and second actuator segments 730, 732, including the leads and/or connections, can be formed as discussed herein.

In one embodiment, the first and second actuator segments 730, 732 are configured to allow a first predetermined section 778 of the elongate body 724 adjacent the distal end 728 and a second predetermined section 780 of the elongate body 724 adjacent the proximal end 726 to extend radially from the common axis 776. In the present embodiment, the predetermined sections 778, 780 include segments 782 that can extend radially from the common axis 776. For example, the segments 782 can flare radially in a symmetrical pattern from the common axis 776 in the first and second predetermined positions (FIGS. 7B and 7C). The segments 782, can be actuated by the first and second actuator segments 730, 732 according to embodiments described herein. In one embodiment, the segments 782 can be formed from the elongate body 724 by cutting and/or dividing the elongate body 724 into the desired shape of the segment 782. Other patterns for the first and second predetermined positions are also possible.

In some embodiments, the closure device 722 can have an elongate body 724 that includes a first actuator segment 730 and a second actuator segment 732 formed from a shape memory alloy, where the first predetermined section 778 and second predetermined section 780 extend radially from the common axis 776. For example, the closure device 722 can include a sheath holding the closure device in a position as shown in FIG. 7A. As the sheath is removed, and the distal end 728 is exposed, and the segments 782 on the first predetermined section 778 can extend radially from the common axis 776 as shown in FIG. 7B. Further, as the sheath is removed completely, the segments 783 on the second predetermined section 778 can also extend radially from the common axis 778 as shown in FIG. 7C.

Figure 8:
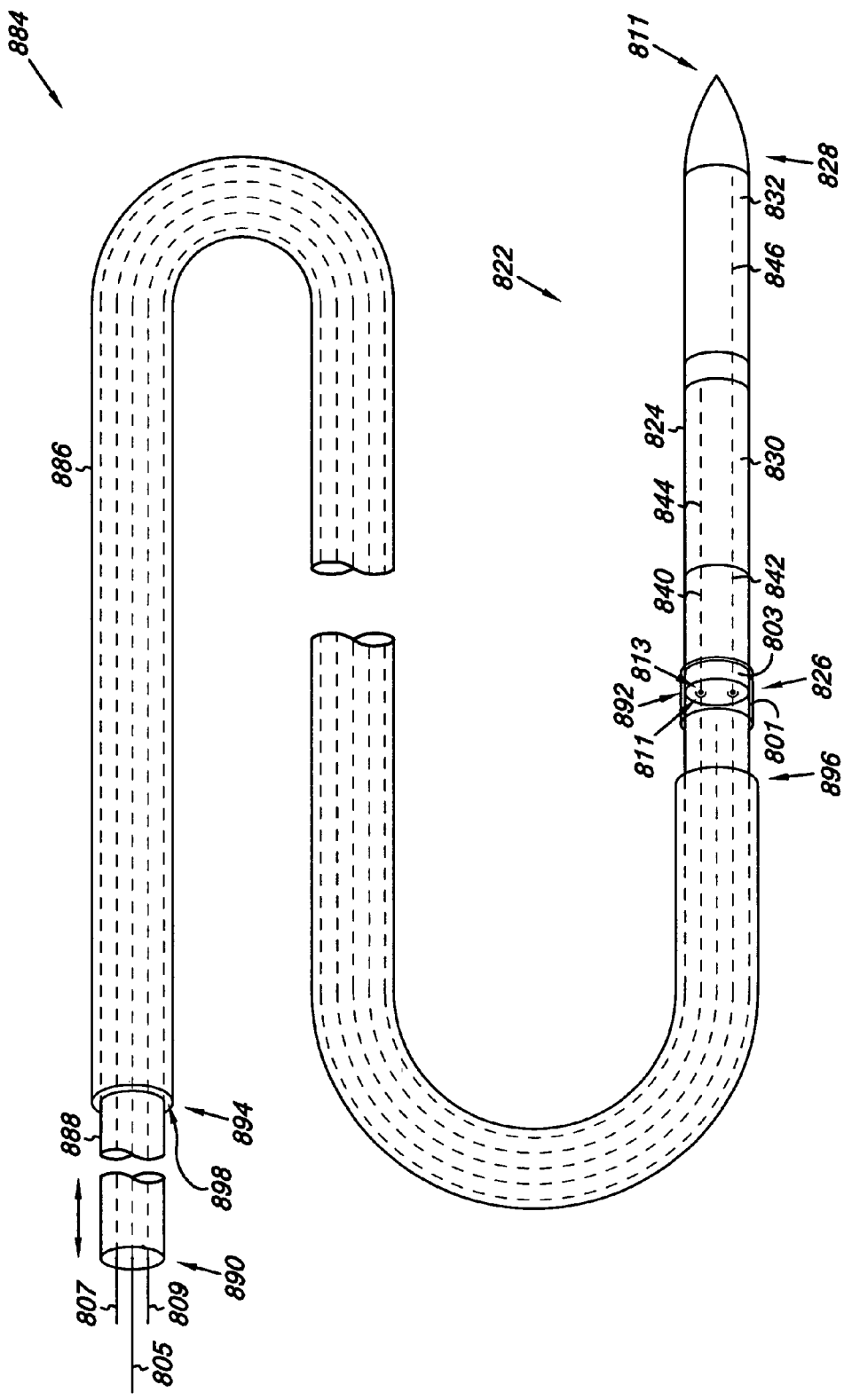
FIG. 8 illustrates an embodiment of a system that includes a closure device according to the present disclosure.

FIG. 8 illustrates an embodiment of a system 884 that includes a guide catheter 886, a delivery catheter 888 and a closure device 822 according to embodiments of the present disclosure. The delivery catheter 888 includes a first end 890 and a second end 892. The guide catheter 886 includes a proximal end 894 and a distal end 896 with a lumen 898 extending through the ends 894, 896. The lumen 898 is sized to allow for the delivery catheter 888 and the closure device 822 to move through the guide catheter 886. The guide catheter 886 also provides lateral support for the delivery catheter 888 when positioned in the lumen 898. This lateral support allows longitudinal forces applied at the first end 890 to be better transferred through the delivery catheter 888 in advancing the closure device 822.

In one embodiment, the delivery catheter 888 is positioned at least partially within and can move longitudinally in the lumen 898 of the guide catheter 886. In one embodiment, the guide catheter 886 can have a predetermined shape that allows the delivery catheter 888 and/or the closure device 822 to extend from the distal end 896 of the guide catheter 886 in a suitable position relative the tissues of a septal defect. As illustrated, the first end 890 of the delivery catheter 888 extends beyond the proximal end 894 of the guide catheter 886 to allow for a person to operate the system 884 as discussed herein. As will be appreciated, the predetermined shape for the delivery catheter 888 will be dependent upon the physiology in the region of the septal defect.

As discussed herein, the closure device 822 can be implanted in several different ways depending on the configuration and material used in forming the closure device 822. For example, when the elongate body 824 of the closure device 822 includes the use of a SMP for the actuator segments 830 and 832, the elongate body 824 can include the conductive elements 840 and 842 and the resistive heating elements 844 and 846, as discussed herein.

In one embodiment, the closure device 822 can be releasably coupled to the delivery catheter 888. For example, the system 884 can include a coupling sleeve 801 that releasably joins the guide catheter 888 and the coupling device 822. In one embodiment, the coupling sleeve 801 can be joined to the guide catheter 886 and/or extend from the distal end 896 to present a socket 803 into which the proximal end 826 and at least a portion of the elongate body 824 can fit. In one embodiment, the coupling sleeve 801 is secured to the guide catheter 888 through the use of an adhesive. Alternatively, the coupling sleeve 801 is an extension of the same material forming the guide catheter 888.

In one embodiment, the coupling sleeve 801 can be used to releasably compress around and secure the closure device 822 to the guide catheter 888. The coupling sleeve 801 can be formed with, for example, an SMP and/or an EAP, or other material, which can allow the size of the socket to increase, thereby allowing the coupling device 822 to be released from the delivery catheter 888. Electrical current for either heating an SMP and/or for delivery across an EAP can be provided by lead 805.

In one embodiment, the delivery catheter 888 can further include a first conductor lead 807 and a second conductor lead 809. In one embodiment, the conductor leads 807, 809 allow for electrical current to be passed to the conductive elements 840, 842 and the resistive heating elements 844, 846 in the elongate body 824. In one embodiment, the first and second conductor leads 807, 809 include a distal end 811 that is releasably coupled to the conductive elements 840, 842. In one embodiment, the conductive elements 840, 842 can include an end 813 that is shaped to releasably engage the distal end 811 of the leads 807, 809. For example, the end 813 of the conductive elements 840, 842 can have a spherical shape (i.e., a ball shape) that releasably engages the distal end 811 of the leads 807, 809 configured as a socket (a ball and socket design). Electrical current can then be supplied through the leads 807, 809 to the resistive heating elements 844, 846 in the elongate body 824. In one embodiment, the ball and socket design allows the leads 807, 809 and conductor elements 840, 842 to release from each other when the coupling sleeve 801 is used to release the closure device 822.

In one embodiment, the coupling sleeve 801 provides a compressive force around at least a portion of the elongate body 824 of the closure device 822 that is sufficient to keep the delivery catheter 888 and the closure device 822 joined until such time as the used elects to release the catheter 888 and device 822. In one embodiment, the compressive force is sufficient to keep the catheter 888 and device 822 joined as, for example, a pulling force is applied through the delivery catheter 888 to the device 822. In an additional embodiment, the surfaces of the catheter 888 and device 822 that engage in the socket 803 can include one or more surfaces that help in joining the two structures. For example, the surface of the socket 803 could include a ridge that releasably engages a corresponding channel in the elongate body 824 of the device 822. Other such structures and/or configurations are possible.

As will be appreciated, the present embodiment is not limited to the closure device 822 illustrated in FIG. 8. Other embodiments of the closure device 822 as discussed herein can be used in conjunction with the delivery catheter 888.

Radiopaque markers can also be included on the closure device 822, the guide catheter 886 and/or the delivery catheter 888. Radiopaque markers can include those having a distinctive shape associated with a predefined portion of the closure device 822, the guide catheter 886 and/or the delivery catheter 888. This allows the operator to better position the catheters 886, 888 and/or the closure device 822 in the patient. Radiopaque markers can include those made of gold, barium sulfate, bismuth trioxide, bismuth carbonate, tungsten, tantalum, or the like.

As will be appreciated, the guide catheter 886, the delivery catheter 888, and the elongate body 824 of the closure device 822 can be formed of a flexible material having sufficient wall strength to resist bending when moved through the vasculature. In one embodiment, suitable flexible materials include, but are not limited to, medical grade polymers and/or copolymers, such as polypropylene, polystyrene, polyurethane, polyvinylchloride, polyethylene, polyetheretherketone, polyetherimide, polyamides, polycarbonate, biodegradables and combinations thereof. Other medical grade polymers, metals, and metal alloys for the above applications are also possible.

In addition, the leads 807, 809 can be a metal or metal alloy. Examples of such metals and metal alloys include, but are not limited to, those provided herein. Other metal and metal alloys are also possible.

To implant the closure device 822 of the present embodiment, the guide catheter 886 can be advanced through, for example, the superior or inferior vena cava to position the distal end 896 in the right atrium of the heart. Other access points and/or locations for positioning the guide catheter 886 are possible. The closure device 822 and the delivery catheter 888 can then be advanced through the lumen 898 of the guide catheter 886 to be position in the right atrium. The second end 892 of the delivery catheter 888 and/or the distal end 828 of the closure device 822 can then be positioned adjacent the tissue of the septal defect, such as the SS and SP of a PFO.

The distal end 828 along with the elongate body 824 of the closure device 822 can then be moved through the tissues of the septal defect to position the distal end 828 and the proximal end 826 on opposite sides of the tissues. In one embodiment, the elongate body 824 includes a tip 811 having a point that can pierce tissues of the septal defect. In one embodiment, piercing the tissues of the septal defect can be accomplished by applying a pushing force from the distal end 826 through the elongate body 824 to the distal end 828.

For the present embodiment, the closure device 822 can be advanced across the tissues to position the first actuator segment 830 and the second actuator segment 832 across the septal defect. The first actuator segment 830 on the elongate body 824 can then be activated, as discussed herein, to direct the tip 811 and the first predetermined portion of the elongate body 824 back towards the septal defect. The tip 811 and the distal end 828 can then be moved back through the tissues of the septal defect so as to position at least a portion of the second actuator segment 832 on the opposite side of the septal defect relative the first actuator segment 830. In one embodiment, this can be accomplished by pulling the closure device 822 through the use of the delivery catheter 888:

The second actuator segment can then be activated, as discussed herein, on the elongate body to direct the second predetermined portion of the elongate body towards the PFO. The first and second predetermined portions of the elongate body 824 can then act to secure the elongate body to the PFO.

In one embodiment, the elongate body 824 can form a loop structure, as discussed herein, that is used to secure the elongate body 824 to opposite sides of the septal defect tissues. Alternatively, the elongate body 824 can form the radially extending shapes (e.g., spirals or other geometric shapes) that extend towards each other on opposite tissue surfaces (e.g., a first side and a second side) of the septal defect.

As will be appreciated, the description of system 884 could also be used with the closure device illustrated in FIGS. 3A-3C, where the system 884 would include additional leads and actuator segments as needed.

Figure 9:
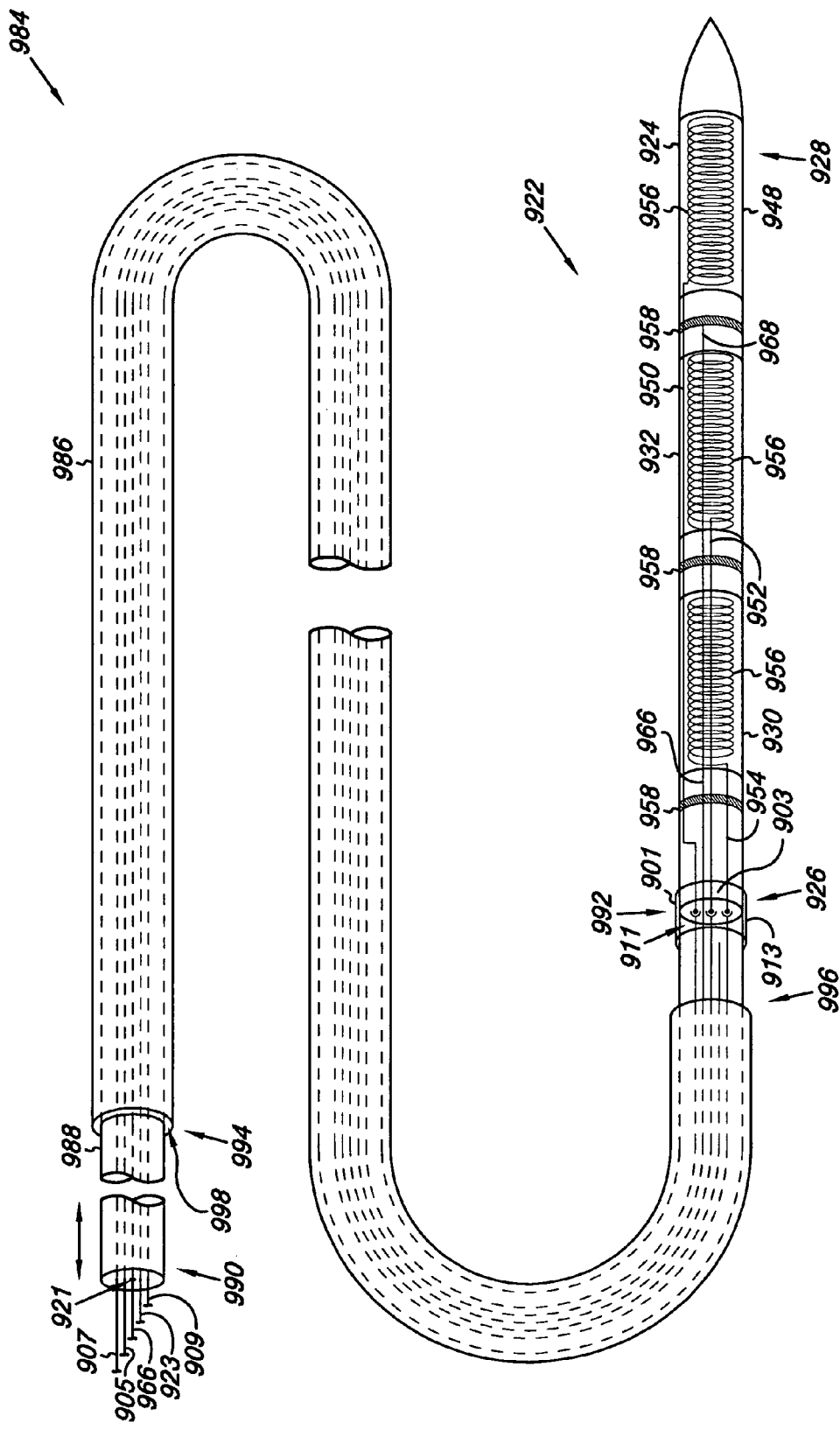
FIG. 9 illustrates an embodiment of a system that includes a closure device according to the present disclosure.

FIG. 9 illustrates an embodiment of a system 984 that includes the guide catheter 986, the delivery catheter 988, and the closure device 922 according to the present disclosure. The closure device 922 can be similar to the closure device as described for FIG. 4 herein. As discussed above, the delivery catheter 988 includes the first and second end 990, 992, and the guide catheter 986 includes the proximal end 994 and the distal end 996 with the lumen 998 extending through the ends 994, 996.

In the present embodiment, the closure device 922 includes the elongate body 924 with proximal end 926, distal end 928, and the first, second and third actuator segment 930, 932 and 948. The closure device 922 further includes leads 950, 952 and 954 each coupled to electrode 956 (e.g., a cathode), as discussed herein, that can be used to supply electrical current to the EAP of each of the first, second and third actuator segments 930, 932, and 948.

As discussed, the elongate body 924 can further include the lumen extending from the proximal end 926 to at least the first, second, and third actuator segments 930, 932, and 948. The system 984 further includes the positionable lead 966, as discussed herein, that extends through and can be moved within the lumen to allow electrical current to be conducted through the EAP of the first, second, and third actuator segments 930, 932, and 948 using electrode 956. The closure device 922 further includes the second electrode 958, as discussed herein, where the positionable lead 966 can be moved within the lumen to allow at least the distal end and/or a portion of the lead 966 adjacent the end make contact with the portion of the second electrode 958.

In the present embodiment, the delivery catheter 988 further includes a lumen 921 that extends through the first end 990 and the second end 992 to join with the lumen of the elongate body 924. The positionable lead 966 can extend and move through the lumen 921 to the lumen of the elongate body 924, as discussed herein, to make electrical contact with the second electrodes 958.

In one embodiment, the closure device 922 can be releasably coupled to the delivery catheter 988. For example, the system 984 can include the coupling sleeve 901 with socket 903 and lead 905, as discussed herein, which releasably joins the guide catheter 988 and the coupling device 922.

In one embodiment, the delivery catheter 988 can further include the first conductor lead 907, the second conductor lead 909, and a third conductor lead 923. In one embodiment, the conductor leads 907, 909, and 923 allow for electrical current to be passed to the leads 950, 952 and 954 in the elongate body 924. In one embodiment, the leads 950, 952 and 954 include a distal end 911 that is releasably coupled to the conductor leads 907, 909, and 923. In one embodiment, the conductor leads 907, 909, and 923 can include an end 913 that is shaped to releasably engage the distal end 811 of the leads 907, 909 and 923. Examples include the ball and socket design discussed herein. Electrical current can then be supplied through the leads 907, 909 and 923 to electrodes 956.

Radiopaque markers can also be included on the closure device 922, the guide catheter 986 and/or the delivery catheter 988, as discussed herein. In addition, the guide catheter 986, the delivery catheter 988, and the elongate body 924 of the closure device 922 can be formed of a flexible material, as discussed herein, having sufficient wall strength to resist bending when moved through the vasculature. In addition, the leads 907, 909 and 923 can be a metal or metal alloy. Examples of such metals and metal alloys include, but are not limited to, those provided herein. Other metal and metal alloys are also possible.

Figure 10:
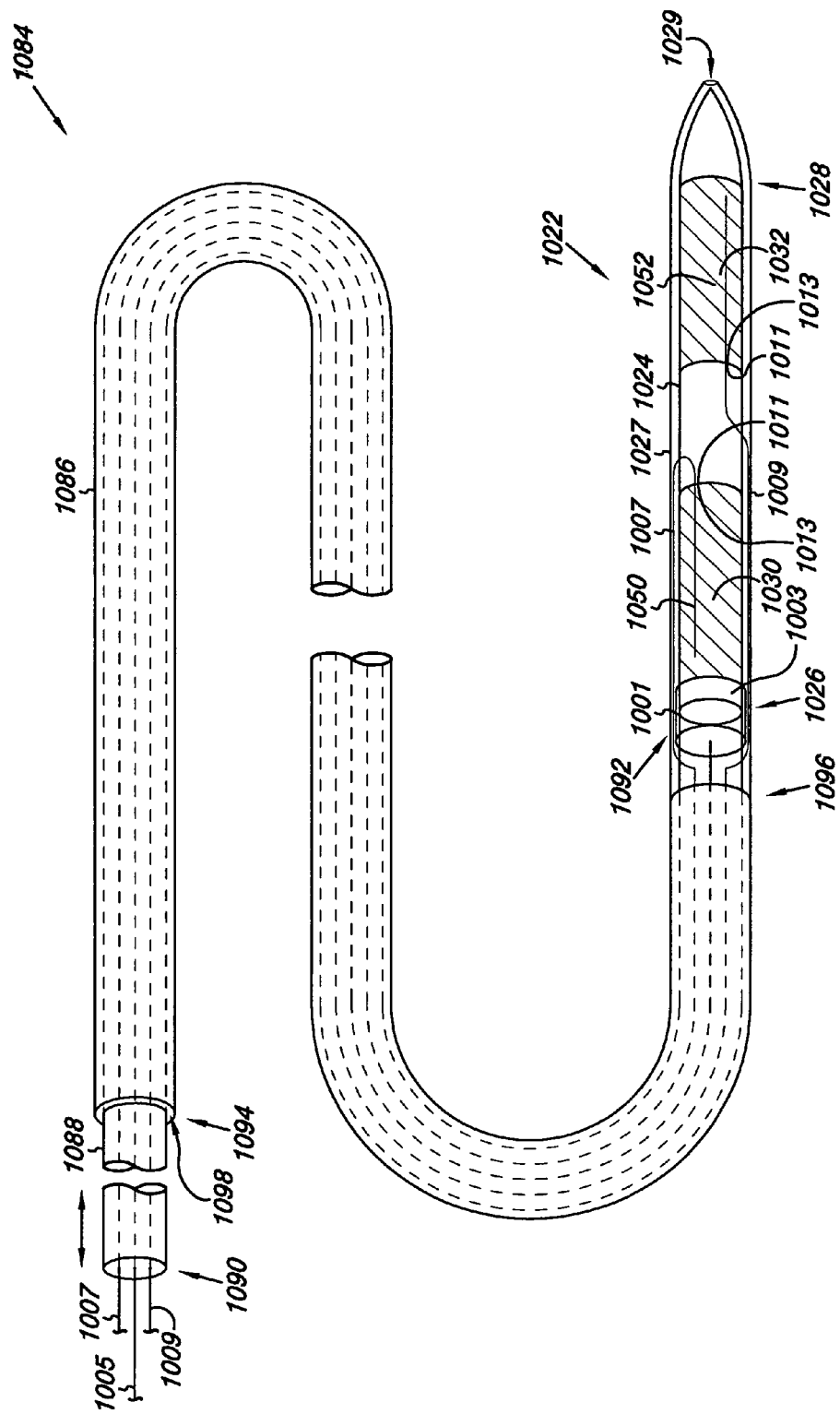
FIG. 10 illustrates an embodiment of a system that includes a closure device according to the present disclosure.

FIG. 10 illustrates an embodiment of a system 1084 that includes the guide catheter 1086, the delivery catheter 1088 and the closure device 1022 according to the present disclosure. In the present embodiment, the closure device 1022 is as described for FIGS. 6A-6C. The description of system 1084, however, could also be used with the closure device described in any one of those illustrated in FIGS. 5A-5C and/or 7A-7C.

As discussed above, the delivery catheter 1088 includes the first and second end 1090, 1092, and the guide catheter 1086 includes the proximal end 1094 and the distal end 1096 with the lumen 1098 extending through the ends 1094, 1096. As illustrated, the delivery catheter 1088 and the closure device 1022 can be housed within a portion 1027 of the guide catheter 1086. In one embodiment, the distal end 1096 of the guide catheter 1086 includes a tip that is sufficiently sharp to allow it to pierce the tissues of a septal defect. The distal end 1096 also defines an opening 1029 that allows the closure device 1022 to pass there through during its delivery across a septal defect. In one embodiment, the opening 1029 can expand to allow the closure device 1022 to be moved from the guide catheter 1086 as a pushing force is applied through the delivery catheter 1088.

In the present embodiment, the closure device 1022 includes the elongate body 1024 with proximal end 1026, distal end 1028, and the first and second actuator segment 1030, 1032. The closure device 1022 further includes leads 1050, 1052 each releasably coupled to the first and second actuator segments 1030, 1032, respectively. As illustrated, the leads 1050, 1052 releaseably couple to the actuator segments 1030, 1032 in a mid-region of the elongate body 1024. In one embodiment, this configuration allows the first and second actuator segments 1030, 1032 to undergo their radial expansion (i.e., movement), as discussed herein, without interfering with their releasable connections to the leads 1050, 1052.

In one embodiment, the closure device 1022 can be releasably coupled to the delivery catheter 1088, as discussed herein. For example, the system 1084 can include the coupling sleeve 1001 with socket 1003 and lead 1005, as discussed herein, which releasably joins the guide catheter 1088 and the coupling device 1022.

In one embodiment, the delivery catheter 1088 can further include the first conductor lead 1007 and the second conductor lead 1009 that allow for electrical current to be passed to the leads 1050 and 1052 in the elongate body 1024. In one embodiment, the leads 1050 and 1052 include a distal end 1011 that is releasably coupled to the conductor leads 1007 and 1009. In one embodiment, the conductor leads 1007 and 1009, can include an end 1013 that is shaped to releasably engage the distal end 1011 of the leads 1007 and 1009. Examples include the ball and socket design discussed herein.

Radiopaque markers can also be included on the closure device 1022, the guide catheter 1086 and/or the delivery catheter 1088, as discussed herein. In addition, the guide catheter 1086, the delivery catheter 1088, and the elongate body 1024 of the closure device 1022 can be formed of a flexible material, as discussed herein, having sufficient wall strength to resist bending when moved through the vasculature. In addition, the leads 1007 and 1009 can be a metal or metal alloy. Examples of such metals and metal alloys include, but are not limited to, those provided herein. Other metal and metal alloys are also possible.

In a further embodiment, the elongate body and/or the actuator segment as provided herein can include one or more therapeutic agents. In one embodiment, the one or more therapeutic agents can be integrated into the material(s) used to form the elongate body and/or the actuator segment and/or coated on the surface of the elongate body and/or the actuator segment. The one or more therapeutic agents can then leach and/or be released from the elongate body and/or the actuator segment once it is applied. The therapeutic agents can be included to promote and/or accelerate endothelialization.

Examples of therapeutic agents include, but are not limited to, pharmaceutically acceptable agents such as non-genetic therapeutic agents, a biomolecule, a small molecule, or cells. Exemplary non-genetic therapeutic agents include anti-thrombogenic agents such as heparin, heparin derivatives, prostaglandin (including micellar prostaglandin E1), urokinase, and PPack (dextrophyenylalanine proline arginine chloromethylketone); anti-proliferative agents such as enoxaprin, angiopenptin, sirolimus (rapamycin), tacrolimus, everolimus monoclonal antibodies capable of blocking smooth muscle cell proliferation, hirudin, and acetylsalicylic acid; anti-inflammatory agents such as dexamethasone, rosiglitazone, prenisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl)ethyleneglycol-N,N,N',N'-tetraacetic acid and mixtures thereof; antibiotics such as gentamycin rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; inhibitors of heat shock proteins such as geldanamycin; and any combinations and prodrugs of the above.

Exemplary biomolecules includes peptides, polypeptides and proteins; oligonucleotides; nucleic acids such as double or single stranded DNA (including naked and cDNA), RNA, antisense nucleic acids such as antisense DNA and RNA, small interfering RNA (siRNA), and riobozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedghog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor, and insulin like growth factor. A non-linear example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin−) cells including Lin−CD34−, Lin−CD34+, Lin−cKit+, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

The therapeutic agents may be combined to the extent such combination is biologically compatible.

As will be appreciated, the embodiments of the present disclosure can be used in different combinations and ways in occluding a septal defect. For example, two or more of the closure devices could be used to treat a septal defect. In one embodiment, each of the two or more of the closure devices could be used alone. Alternatively, the two or more of the closure devices could be used in such a way that they interact with each other. For example, a first closure device could be introduced from a first side of a septal defect. A second closure device could then be introduced from a second side of the septal defect. In one embodiment, the closure devices could then be secured to each other (e.g., the elongate bodies entwine, cross and/or lock together) as they occlude the septal defect. Other combinations are also possible.

In an additional embodiment, the embodiments of the present disclosure can also include the use of a second catheter. In one embodiment, the second catheter could include extendable members that could be used to engage the distal end of the closure device. In one embodiment, the second catheter can be used to puncture the tissues of the septal defect where it can then be used to engage the closure device and draw the device back across the tissues of the septal defect. Once engaged, the second catheter can then be used to help draw the closure device into its closed loop configuration.

In a further embodiment, additional structures and configurations exist that can allow the delivery catheter, the closure device and the associated leads and connectors to disengage. As discussed, one embodiment includes the use of a socket to releasably couple the closure device and the delivery catheter where the electrical connection is made through a ball and socket configured connection. In an additional embodiment, the electrical connection could be made with connectors that can uncouple by a twisting action provided through the delivery catheter. Alternatively, the releasable leads and/or connectors could have a cage configuration (e.g., a loop configuration) whose shape can be changed (e.g., the opening of the loop enlarges) to allow the leads to release from the cage. Other configurations are also possible.

While the present disclosure has been shown and described in detail, changes and modifications may be made without departing from the scope of the disclosure. As such, that which is set forth in the foregoing description and accompanying drawings is offered by way of illustration only and not as a limitation. In addition, various features may have been grouped together in several embodiments for the purpose of streamlining the disclosure. This method of disclosure is not to be interpreted as reflecting an intention that the embodiments of the disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

We claim:

1. A closure device, comprising:
an elongate body having a proximal end and a distal end;
a first actuator segment associated with the elongate body; and
a second actuator segment associated with the elongate body, where the first actuator segment and the second actuator segment include a shape memory polymer, where the elongate body includes a first conductive element extending from the proximal end to the first actuator segment and a second conductive element extending from the proximal end to the second actuator segment, where the first conductive element provides thermal energy to the shape memory polymer of the first actuator to cause the first actuator segment to bend the elongate body to a first predetermined position and the second conductive element provides thermal energy to the shape memory polymer of the second actuator to cause the second actuator segment to bend the elongate body to a second predetermined position, the distal end and the proximal end being more closely positioned in the second predetermined position than in the first predetermined position, and where the elongate body defines a longitudinal slit adjacent the proximal end that receives the distal end of the elongate body when in the second predetermined position.

2. The closure device of claim 1, wherein the distal end extends towards the proximal end when the elongate body is in the first predetermined position.

3. A closure device, comprising:
an elongate body having a proximal end and a distal end;
a first actuator segment associated with the elongate body; and
a second actuator segment associated with the elongate body, where the first actuator segment and the second actuator include an electroactive polymer, where the elongate body includes a first lead extending from the proximal end to the first actuator segment and a second lead extending from the proximal end to the second actuator segment where the first lead supplies electric current to the electroactive polymer of the first actuator segment to cause the first actuator segment to bend the elongate body to a first predetermined position and the second lead supplies electric current to the electroactive polymer of the second actuator to cause the second actuator segment to bend the elongate body to a second predetermined position, the distal end and the proximal end being more closely positioned in the second predetermined position than in the first predetermined position, and where the elongate body defines a longitudinal slit adjacent the proximal end that receives the distal end of the elongate body when in the second predetermined position.

4. The closure device of claim 3, wherein the distal end extends towards the proximal end when the elongate body is in the first predetermined position.

5. A closure device, comprising:
an elongate body having a proximal end and a distal end;
a first actuator segment associated with the elongate body; and
a second actuator segment associated with the elongate body, where the first actuator segment and the second actuator include an electroactive polymer, where the elongate body includes a lumen extending from the proximal end to the first and second actuator segments, and a positionable lead extending through the lumen, where the positionable lead moves within the lumen to conduct electrical current through the electro-active polymer of the first and second actuator segments, where the first actuator segment bends the elongate body to a first predetermined position and the second actuator segment bends the elongate body to a second predetermined position, the distal end and the proximal end being more closely positioned in the second predetermined position than in the first predetermined position, and where the elongate body defines a longitudinal slit adjacent the proximal end to receive the distal end of the elongate body when in the second predetermined position.

6. The closure device of claim 5, wherein the distal end extends towards the proximal end when the elongate body is in the first predetermined position.

* * * * *